(12) United States Patent
Vogelstein et al.

(10) Patent No.: US 10,144,971 B2
(45) Date of Patent: Dec. 4, 2018

(54) GENES FREQUENTLY ALTERED IN PANCREATIC NEUROENDOCRINE TUMORS

(75) Inventors: Bert Vogelstein, Baltimore, MD (US); Kenneth W Kinzler, Baltimore, MD (US); Victor Velculescu, Dayton, MD (US); Luis Diaz, Ellicott City, MD (US); Nikolas Papadopoulos, Towson, MD (US); Yuchen Jiao, Columbia, MD (US); Ralph Hruban, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 248 days.

(21) Appl. No.: 13/977,810

(22) PCT Filed: Jan. 4, 2012

(86) PCT No.: PCT/US2012/020199
§ 371 (c)(1),
(2), (4) Date: Oct. 24, 2013

(87) PCT Pub. No.: WO2012/094401
PCT Pub. Date: Jul. 12, 2012

(65) Prior Publication Data
US 2014/0045881 A1     Feb. 13, 2014

Related U.S. Application Data

(60) Provisional application No. 61/429,666, filed on Jan. 4, 2011.

(51) Int. Cl.
| | |
|---|---|
| C12Q 1/68 | (2018.01) |
| C12P 19/34 | (2006.01) |
| C12Q 1/6886 | (2018.01) |
| G01N 33/574 | (2006.01) |

(52) U.S. Cl.
CPC ..... *C12Q 1/6886* (2013.01); *G01N 33/57438* (2013.01); *C12Q 2600/106* (2013.01); *C12Q 2600/112* (2013.01); *C12Q 2600/118* (2013.01); *C12Q 2600/156* (2013.01); *G01N 2800/52* (2013.01)

(58) Field of Classification Search
None
See application file for complete search history.

(56) References Cited

PUBLICATIONS

Lucentini, The Scientist, 2004, p. 20.*
Pennisi, Science, 1998, vol. 281, 1787-1789.*
Hegele, Arterioscler. Thromb. Vasc. Biol., 2002, 22:1058-1061.*
Missiaglia, E., et al., "Pancreatic endocrine tumors: Expression profiling evidences a role for AKT-mTOR pathway," Journal of Clinical Oncology, Jan. 10, 2010, pp. 245-255, vol. 28, No. 2.
Luttges, J., et al., "The K-ras mutation pattern in pancreatic ductal adenocarcinoma usually is identical to that in associated normal, hyperplastic, and metaplastic ductal epithelium," Cancer, Apr. 15, 1999, pp. 1703-1710,vol. 85, No. 8.
Corbo, V., et al., "MEN1 in pancreatic endocrine tumors: analysis of gene and protein status in 169 sporadic neoplasms reveals alterations in the vast majority of cases," Endocrine-Related Cancer, Aug. 16, 2010, pp. 771-783, vol. 17.
Guerra, C., et al. "Chronic pancreatitis is essential for induction of pancreatic ductal adenocarcinoma by K-Ras oncogenes in adult mice," Cancer Cell, Mar. 2007, pp. 291-302, vol. 11.
Jiao, Y., et al., "DAXX/ATRX, MEN1, and mTOR pathway genes are frequently altered in pancreatic neuroendocrine tumors," Science, Mar. 4, 2011, pp. 1199-1203, vol. 331, No. 6021.
International Search Report dated Aug. 29, 2012 in PCT/US2012/020199.
Fredrich et al., "Neuronal subtype identity in the rat auditory brainstem as defined by molecular profile and axonal projection," *Exp Brain Res* 195, 241 (2009).
Ekeblad et al., "Prognostic Factors and Survival in 324 Patients with Pancreatic Endocrine Tumor Treated at a Single Institution," *Clin Cancer Res* 14, 7798 (2008).
Francalanci et al., "Malignant Pancreatic Endocrine Tumor in a Child With Tuberous Sclerosis," *Am J Surg Pathology* 27, 1386 (2003).
Corbo el al., "MEN1 in pancreatic endocrine tumors: analysis of gene and protein status in 169 sporadic neoplasms reveals alterations in the vast majority of cases," *Endocr Relat Cancer* 17, 771 (2010).
Capelli et al., "Endocrine Neoplasms of the Pancreas: Pathologic and Genetic Features," *Arch Pathol Lab Med* 133, 350 (2009).
Chung et al., "Localization of Putative Suppressor Loci by Genome-wide Allelotyping in Human Pancreatic Endocrine Tumors," *Cancer Res* 58, 3706 (1998).
Floridia et al.,"Chromosomal alterations detected by comparative genomic hybridization in nonfunctioning endocrine pancreatic tumors," *Cancer Genet. Cytogenet.* 156, 23 (2005).
W. Hu et al., Genes Cancer 1, 360 (2010).

(Continued)

*Primary Examiner* — Sarae L Bausch
(74) *Attorney, Agent, or Firm* — Fish & Richardson P.C.

(57) ABSTRACT

Pancreatic Neuroendocrine Tumors (PanNETs) are a rare but clinically important form of pancreatic neoplasia. To explore the genetic basis of PanNETs, we determined the exomic sequences of ten non-familial PanNETs and then screened the most commonly mutated genes in 58 additional PanNETs. Remarkably, the most frequently mutated genes specify proteins implicated in chromatin remodeling: 44% of the tumors had somatic inactivating mutations in MEN-1, which encodes menin, a component of a histone methyltransferase complex; and 43% had mutations in genes encoding either of the two subunits of a transcription/chromatin remodeling complex consisting of DAXX (death-domain associated protein) and ATRX (alpha thalassemia/mental retardation syndrome X-linked). Clinically, mutations in the MEN1 and DAXX/ATRX genes were associated with better prognosis. We also found mutations in genes in the mTOR (mammalian target of rapamycin) pathway in 14% of the tumors, a finding that could potentially be used to stratify patients for treatment with mTOR inhibitors.

22 Claims, 28 Drawing Sheets
Specification includes a Sequence Listing.

(56) References Cited

PUBLICATIONS

S. Jones et al., "Core Signaling Pathways in Human Pancreatic Cancers Revealed by Global Genomic Analyses," *Science* 321, 1801 (2008).
Parsons et al., "Colorectal cancer: Mutations in a signalling pathway," *Nature* 436, 792 (2005).
Guertin et al., "Defining Role of mTOR in Cancer," *Cancer Cell* 12, 9 (2007).
Shaw et al., "Ras, PI(3)K and m TOR signalling controls tumour cell growth," *Nature* 441, 424 (2006).
Hughes el al., "Menin Associates with a Trithorax Family Histone Methyltransferase Complex and with the Hoxc8 Locus," *Mol Cell* 13, 587 (2004).
Yokoyama et al., "Leukemia Proto-Oncoprotein MLL Forms a SET1-Like Histone Methyltransferase Complex with Menin to Regulate Hox Gene Expression," *Mol Cell Biol* 24, 5639 (2004).
Kim et al., "Menin, a Tumor Suppressor, Represses JunD-Mediated Transcriptional Activity by Association with an mSin3A-Histone Deacetylase Complex," *Cancer Res.* 63, 6135 (2003).
Agarwal et al., "Menin Interacts with the API Transcription Factor JunD and Represses JunD-Activated Transcription," *Cell* 96, 143 (1999).
Lewis et al., "DAXX is an H3.3-specific jistone chaperone and cooperates with ATRX in replication-independaent chromatin assembly at telomeres," *Proc Natl Acad Sci US A* 107, 14075 (2010).

\* cited by examiner

TABLE 1. MUTATION IN MEN1, DAXX, ATRX, PTEN, TSC2, PIK3CA, AND TP53 IN HUMAN PANCREATIC NEUROENDOCRINE TUMORS.

| SAMPLE# | GENE | TRANSCRIPT ACCESSION | NUCLEOTIDE (GENOMIC)* | NUCLEOTIDE (cDNA) | AMINO ACID (PROTEIN) | MUTATION TYPE |
|---|---|---|---|---|---|---|
| PanNET3PT | ATRX | CCDS14434.1 | g.chrX:76716462G>A(hom) | c.6235C>T(hom) | p.R2079X | NONSENSE |
| PanNET5PT | ATRX | CCDS14434.1 | g.chrX:76742636G>A | c.5620C>T | p.Q1874X | NONSENSE |
| PanNET13PT | ATRX | CCDS14434.1 | g.chrX:76741560delA | c.5932delT | fs | INDEL |
| PanNET27PT | ATRX | CCDS14434.1 | g.chrX:76700959_76700962delATAA | c.6338_6341delTTAT | fs | INDEL |
| PanNET35PT | ATRX | CCDS14434.1 | g.chrX:76906893_76806909delAATTTCTTCTAAAAGCA | c.3824_3840delTGCTTTTAGAAGAAATT | fs | INDEL |
| PanNET52PT | ATRX | CCDS14434.1 | g.chrX:76796337_76796340delGTTT | c.4221_4224delAAAG | fs | INDEL |
| PanNET59PT | ATRX | CCDS14434.1 | g.chrX:76761014C>A | c.5364G>T | p.Q1788H | MISSENSE |
| PanNET78PT | ATRX | CCDS14434.1 | g.chr6:76665406C>T | c.6829G>A | p.E2277K | MISSENSE |
| PanNET85PT | ATRX | CCDS14434.1 | g.chrX:76794404dupC | c.4414dupG | fs | INDEL |
| PanNET98PT | ATRX | CCDS14434.1 | g.chrX:76700832T>A(hom) | c.6468A>T(hom) | p.Q2156H | MISSENSE |
| PanNET100PT | ATRX | CCDS14434.1 | g.chrX:76762518_76762521delCACT(hom) | c.5270_5272delAGTG(hom) | fs | INDEL |
| PanNET112PT | ATRX | CCDS14434.1 | g.chrX:76826041T>A(hom) | c.1363A>T(hom) | p.K455X | NONSENSE |
| PanNET23PT | DAXX | CCDS4776.1 | g.chr6:33394939delT | c.1976delA | fs | INDEL |
| PanNET31PT | DAXX | CCDS4776.1 | g.chr6:33394935delC(hom) | c.1980delG(hom) | fs | INDEL |
| PanNET44PT | DAXX | CCDS4776.1 | g.chr6:33397319delG | c.2120delC | fs | INDEL |
| PanNET56PT | DAXX | CCDS4776.1 | g.chr6:33397319delG | c.2111delC | fs | INDEL |
| PanNET77PT | DAXX | CCDS4776.1 | g.chr6:33396614G>A | c.916C>T | p.R306X | NONSENSE |
| PanNET84PT | DAXX | CCDS4776.1 | g.chr6:33395309delG | c.1766delC | fs | INDEL |
| PanNET87PT | DAXX | CCDS4776.1 | g.chr6:33397141A>C | c.389T>G | p.L130R | MISSENSE |
| PanNET93PT | DAXX | CCDS4776.1 | g.chr6:33396641C>G | c.889G>C | p.A297P | MISSENSE |
| PanNET94PT | DAXX | CCDS4776.1 | g.chr6:33394872_33394873insA | c.2042_2043insT | fs | INDEL |
| PanNET95PT | DAXX | CCDS4776.1 | g.chr6:33397221_33397224delCGCC | c.306_309delAGGCG | fs | INDEL |
| PanNET96PT | DAXX | CCDS4776.1 | g.chr6:33396167delC | c.1219delG | fs | INDEL |
| PanNET97PT | DAXX | CCDS4776.1 | g.chr6:33395638C>A(hom) | c.1393G>T(hom) | p.E465X | NONSENSE |
| PanNET102PT | DAXX | CCDS4776.1 | g.chr6:33397515T>A | c.166A>T | p.K56X | NONSENSE |
| PanNET103PT | DAXX | CCDS4776.1 | g.chr6:33397579delA | c.102delT | fs | INDEL |
| PanNET104PT | DAXX | CCDS4776.1 | g.chr6:33396604_33396605insACT(hom) | c.918_919insAGT(hom) | fs | INDEL |

FROM FIG. 3A

| | | | | |
|---|---|---|---|---|
| PanNET108PT | DAXX | CCDS4776.1 | g.chr6:33395628delT(hom) | fs | INDEL |
| PanNET133PT | DAXX | CCDS4776.1 | g.chr6:33395089C>A(hom) | p.E448X | NONSENSE |
| PanNET3PT | MEN1 | CCDS8083.1 | g.chr11:64331709C>A(hom) | p.G230V | MISSENSE |
| PanNET5PT | MEN1 | CCDS8083.1 | g.chr11:64332046A>G(hom) | p.W188R | MISSENSE |
| PanNET6PT | MEN1 | CCDS8083.1 | g.chr11:64333812_64333826delCACGCTGGAGAGACCC | c.329_345delGGGTGTCTCCAGGCGTG | fs | INDEL |
| PanNET10PT | MEN1 | CCDS8083.1 | g.chr11:64334105_64334108delTCGT(hom) | c.50_53delAGGA(hom) | fs | INDEL |
| PanNET23PT | MEN1 | CCDS8083.1 | g.chr11:64331233_64331234delAG(hom) | c.832_833delCT(hom) | fs | INDEL |
| PanNET29PT | MEN1 | CCDS8083.1 | g.chr11:64334070C>A(hom) | c.88G>T(hom) | p.E30X | NONSENSE |
| PanNET31PT | MEN1 | CCDS8083.1 | g.chr11:64328537G>T | c.1643C>A | p.S548X | NONSENSE |
| PanNET39PT | MEN1 | CCDS8083.1 | g.chr11:64333903_64333999delAGGGATG(hom) | c.159_165delCATCCCT(hom) | fs | INDEL |
| PanNET44PT | MEN1 | CCDS8083.1 | g.chr11:64333955delG | c.203delC | fs | INDEL |
| PanNET45PT | MEN1 | CCDS8083.1 | g.chr11:64330370G>C | c.974C>G | p.P325R | MISSENSE |
| PanNET52PT | MEN1 | CCDS8083.1 | g.chr11:64333876delG | c.282delC | fs | INDEL |
| PanNET57PT | MEN1 | CCDS8083.1 | g.chr11:64334002delG(hom) | c.156delC(hom) | fs | INDEL |
| PanNET59PT | MEN1 | CCDS8083.1 | g.chr11:64329234G>A | c.1213C>T | p.Q405X | NONSENSE |
| PanNET61PT | MEN1 | CCDS8083.1 | g.chr11:64334049_64334201delGGAGGCACCAGGTCCGGCTCCTCT CGGCCCAGCTCGGCAGCAGCAAACAGCGGCACCAGTCGCTCGATGGAGC GCAGCGGGAACAGCGCTCTTCTGGGCGGCCCTTCAGCCCCATGGCGGC GGGCCGGTGGGCGGCGGCCTGCAAGGCAAGCCGGGGGAG(hom) | c.1_109delATGGGGCTGAAGGCGGCGCCAGAA GACGGTGTTCCCGCTGCGCTCCATCGACGACG TGGTGCGCCTGTTTGCTGCCGAGCTGGGCCGA GAGGAGCCGGACCTGGTGCTCC(hom) | fs | INDEL |
| PanNET64PT | MEN1 | CCDS8083.1 | g.chr11:64333781delC | c.377delG | fs | INDEL |
| PanNET69PT | MEN1 | CCDS8083.1 | g.chr11:64333291delA | c.1053delT | fs | INDEL |
| PanNET77PT | MEN1 | CCDS8083.1 | g.chr11:64334079delCTGGGCCGCCAGAGGAGACC | c.79_95delCTGGGCCGCCAGAGGAGCC | fs | INDEL |
| PanNET78PT | MEN1 | CCDS8083.1 | g.chr11:64332045C>T | c.563G>A | p.W188X | NONSENSE |
| PanNET83PT | MEN1 | CCDS8083.1 | g.chr11:64333069delG | c.976delC | fs | INDEL |
| PanNET84PT | MEN1 | CCDS8083.1 | g.chr11:64334139G>A | c.19C>T | p.Q7X | NONSENSE |
| PanNET85PT | MEN1 | CCDS8083.1 | g.chr11:64332011_64332012insCTGT | c.596_597insACAG | fs | INDEL |

FROM FIG. 3B

| Sample | Gene | CCDS | Genomic coordinate | cDNA | Protein | Type |
|---|---|---|---|---|---|---|
| PanNET93PT | MEN1 | CCDS8083.1 | g.chr11:64333906_64333909delAGAC | c.245_248delTCT | fs | INDEL |
| PanNET94PT | MEN1 | CCDS8083.1 | g.chr11:64333906_64333909delAGAC | c.245_248delTCT | fs | INDEL |
| PanNET95PT | MEN1 | CCDS8083.1 | g.chr11:64332032delC(hom) | c.576delCG(hom) | fs | INDEL |
| PanNET96PT | MEN1 | CCDS8083.1 | g.chr11:64331269T>C | c.IVS799-2A>G | | SPLICESITE |
| PanNET99PT | MEN1 | CCDS8083.1 | g.chr11:64331938C>A | c.IVS669+1G>T | | SPLICESITE |
| PanNET100PT | MEN1 | CCDS8083.1 | g.chr11:64331940_64331941delCG(hom) | c.667_668delCG(hom) | fs | INDEL |
| PanNET102PT | MEN1 | CCDS8083.1 | g.chr11:64321022G>A | c.506C>T | p.A169V | MISSENSE |
| PanNET108PT | MEN1 | CCDS8083.1 | g.chr11:64331200_64331251delGCAGCCTGGCCACTTCCCTCTACTGACCTTTCCAGATGTCCAGGTCATAGA(hom) | c.815_837delTCTATGACCTGGGACATCTGGA del exon and intron A(hom) | | INDEL |
| PanNET109PT | MEN1 | CCDS8083.1 | g.chr11:64334093A>C | c.65T>G | p.L22R | MISSENSE |
| PanNET10PT | PIK3CA | CCDS43171.1 | g.chr3:180418785G>A | c.1633G>A | p.E45K | MISSENSE |
| PanNET10PT | PTEN | CCDS31238.1 | g.chr10:89706933delG | c.736delG | fs | INDEL |
| PanNET31PT | PTEN | CCDS31238.1 | g.chr10:89682819T>G | c.323T>G | p.L108R | MISSENSE |
| PanNET29PT | PTEN | CCDS31238.1 | g.chr10:89710791insTGACAAGGAATATCTAGTACTTAC TTAA | c.1992_c.1993insTGACAAGGAATATCTAGTA CTTACTTAA | fs | INDEL |
| PanNET96PT | PTEN | CCDS31238.1 | g.chr10:89675287T>C(hom) | c.202T>C(hom) | p.Y68H | MISSENSE |
| PanNET104PT | PTEN | CCDS31238.1 | g.chr10:89701856G>A(hom) | c.494G>A(hom) | p.G165E | MISSENSE |
| PanNET24PT | TP53 | CCDS11118.1 | g.chr17:7518284G>A | c.722C>T | p.S241F | MISSENSE |
| PanNET91PT | TP53 | CCDS11118.1 | g.chr17:7519210delA(hom) | c.445delT(hom) | fs | INDEL |
| PanNET100PT | TP53 | CCDS11118.1 | g.chr17:7520101delT(hom) | c.311delA(hom) | fs | INDEL |
| PanNET2PT | TSC2 | CCDS10458.1 | g.chr16:2070191C>T | c.3422C>T | p.A1141V | MISSENSE |
| PanNET31PT | TSC2 | CCDS10458.1 | g.chr16:2074957G>A | c.4498G>A | p.V1500M | MISSENSE |
| PanNET44PT | TSC2 | CCDS10458.1 | g.chr16:2074337_2074338delTG | c.4113_c.4114delTG | fs | INDEL |
| PanNET70PT | TSC2 | CCDS10458.1 | g.chr16:2078571C>T | c.5383C>T | p.R1795C | MISSENSE |
| PanNET93PT | TSC2 | CCDS10458.1 | g.chr16:2038643C>A | c.26C>A | p.S9X | NONSENSE |
| PanNET112PT | TSC2 | CCDS10458.1 | g.chr16:2076836A>G | c.4952A>G | p.N1651S | MISSENSE |

*COORDINATES REFER TO HUMAN REFERENCE GENOME hg 18 RELEASE (NCBI 36.1, MARCH 2006).
SAMPLES PanNET3, PanNET7, PanNET10, PanNET23, PanNET24, PanNET25, PanNET31, PanNET36, AND PanNET93 WERE USED FOR THE INITIAL (DISCOVERY SET) SCREEN.

FIG. 3C

TABLE S1. SUMMARY OF SEQUENCE ANALYSIS OF PanNETs

|  | AVERAGE | PEN3 TUMOR | PEN3 NORMAL | PEN7 TUMOR | PEN7 NORMAL | PEN10 TUMOR | PEN10 NORMAL |
|---|---|---|---|---|---|---|---|
| BASES IN TARGET REGION | 37,806,033 | 37,806,033 | 37,806,033 | 37,806,033 | 37,806,033 | 37,806,033 | 37,806,033 |
| BASES SEQUENCED (AFTER QUALITY FILTERING) | 8,970,317,625 | 10,417,478,100 | 9,664,077,150 | 6,965,642,100 | 4,815,412,350 | 17,928,374,700 | 17,910,234,450 |
| BASES MAPPED TO GENOME | 7,863,163,110 | 9,228,427,500 | 8,535,293,850 | 6,212,175,525 | 4,302,345,375 | 14,768,113,500 | 14,745,506,475 |
| BASES MAPPED TO TARGETED REGION | 4,565,426,332 | 5,446,170,687 | 5,154,911,336 | 3,456,789,217 | 2,355,600,301 | 8,683,709,467 | 9,597,863,642 |
| AVERAGE # OF READS PER TARGETED BASE | 101 | 118.7 | 122.1 | 83.2 | 59.0 | 169.4 | 210.8 |
| TARGETED BASES WITH AT LEAST 10 READS (%) | 94.8% | 94.7% | 96.3% | 95.4% | 93.9% | 94.8% | 96.9% |
| KNOWN SNPs IDENTIFIED IN TARGETED REGION | 19,488 | 18,862 | 21,493 | 19,602 | 19,645 | 18,021 | 19,582 |
| SOMATIC MUTATIONS IDENTIFIED IN TARGETED REGION | 16 | 17 | | 10 | | 25 | |

| | PEN21 | | PEN23 | | PEN24 | | PEN25 | |
|---|---|---|---|---|---|---|---|---|
| | TUMOR | NORMAL | TUMOR | NORMAL | TUMOR | NORMAL | TUMOR | NORMAL |
| | 37,806,033 | 37,806,033 | 37,806,033 | 37,806,033 | 37,806,033 | 37,806,033 | 37,806,033 | 37,806,033 |
| | 5,901,283,500 | 5,373,124,500 | 8,926,754,250 | 5,826,630,900 | 10,617,815,700 | 10,898,967,300 | 6,477,238,950 | 5,658,681,000 |
| | 5,301,246,225 | 4,801,928,925 | 7,532,781,525 | 5,190,377,475 | 9,468,896,400 | 9,695,813,850 | 5,802,006,600 | 5,037,623,700 |
| | 3,004,915,980 | 2,719,855,819 | 3,999,365,541 | 2,770,896,102 | 5,507,569,855 | 5,868,452,371 | 3,448,164,263 | 2,989,321,562 |
| | 73.0 | 67.9 | 80.9 | 67.5 | 116.2 | 125.8 | 81.4 | 73.1 |
| | 95.7% | 94.9% | 88.1% | 95.4% | 92.7% | 95.0% | 95.7% | 95.4% |
| | 19,365 | 19,391 | 17,513 | 19,646 | 18,353 | 19,569 | 21,301 | 21,391 |
| | 11 | | 23 | | 19 | | 16 | |

FROM FIG. 4A

|  | PEN31 |  | PEN36 |  | PEN93 |  |
| --- | --- | --- | --- | --- | --- | --- |
|  | Tumor | Normal | Tumor | Normal | Tumor | Normal |
|  | 37,806,033 | 37,806,033 | 37,806,033 | 37,806,033 | 37,806,033 | 37,806,033 |
|  | 10,767,268,950 | 11,182,041,450 | 6,256,693,650 | 4,946,709,750 | 10,118,621,400 | 8,753,302,350 |
|  | 9,710,837,925 | 10,003,229,175 | 5,600,819,925 | 4,458,735,675 | 9,032,126,550 | 7,834,976,025 |
|  | 5,622,109,026 | 5,996,227,925 | 3,328,711,814 | 2,705,176,464 | 4,745,325,793 | 3,907,389,468 |
|  | 109.3 | 125.1 | 77.7 | 66.1 | 108.9 | 93.5 |
|  | 92.9% | 95.1% | 95.7% | 95.5% | 95.6% | 95.5% |
|  | 18,556 | 19,578 | 19,255 | 19,309 | 19,611 | 19,711 |
|  | 21 |  | 8 |  | 16 |  |

FROM FIG. 4B

FIG. 4C

TABLE S2. MUTATIONS IDENTIFIED IN THE DISCOVERY SET

| SAMPLE | GENE | TRANSCRIPT ACCESSION | NUCLEOTIDE (GENOMIC)* | NUCLEOTIDE (cDNA) | AMINO ACID (PROTEIN) | MUTATION TYPE |
|---|---|---|---|---|---|---|
| PanNET24PT | ABCA7 | CCDS12055.1 | g.chr19:1002998G>A | c.3020G>A | p.R1007H | MISSENSE |
| PanNET36PT | ABCB4 | CCDS5606.1 | g.chr7:86872595A>G | c.3452T>C | p.I1151T | MISSENSE |
| PanNET23PT | ADAMTS8 | CCDS41732.1 | g.chr11:129766672G>A | c.1600C>T | p.P534S | MISSENSE |
| PanNET31PT | AFMID | CCDS32750.1 | g.chr17:73713668A>T | c.842A>T | p.D281V | MISSENSE |
| PanNET23PT | AHNAK | CCDS31884.1 | g.chr11:62045777C>A | c.12686G>T | p.D4230Y | MISSENSE |
| PanNET31PT | AKAP6 | CCDS9944.1 | g.chr14:32861464G>C | c.4694G>C | p.S1565T | MISSENSE |
| PanNET24PT | ALK | CCDS33172.1 | g.chr2:29270037C>G | c.4420G>C | p.G1474R | MISSENSE |
| PanNET10PT | ANXA8L2 | CCDS7216.1 | g.chr10:47221179G>T(hom) | c.50G>T(hom) | p.S17I | MISSENSE |
| PanNET31PT | ARMC5 | CCDS42155.1 | g.chr16:31381087C>T | c.718C>T | p.R240C | MISSENSE |
| PanNET24PT | ATP6V0A1 | CCDS11426.1 | g.chr17:37910681A>G | c.1418A>G | p.N473S | MISSENSE |
| PanNET3PT | ATRX | CCDS14434.1 | g.chrX:76716462G>A(hom) | c.6235C>T(hom) | p.R2079X | NONSENSE |
| PanNET24PT | BCL9L | CCDS8403.1 | g.chr11:118277917C>T(hom) | c.1745G>A(hom) | p.G582E | MISSENSE |
| PanNET23PT | BCR | CCDS13806.1 | g.chr22:21983976_21983977insCCGG | c.3275_3276insCCGG | fs | INDEL |
| PanNET25PT | BRD1 | CCDS14080.1 | g.chr22:48603492C>T | c.478G>A | p.E160K | MISSENSE |
| PanNET3PT | C21orf58 | CCDS13735.1 | g.chr21:45662467C>T(hom) | c.196G>A(hom) | p.G66R | MISSENSE |
| PanNET24PT | C4orf27 | CCDS3813.1 | g.chr4:170899684_170899686delTTC | c.646_648delGAA | fs | INDEL |
| PanNET10PT | CABIN1 | CCDS13823.1 | g.chr22:22817548_22817549delGC | c.3537_3538delGC | fs | INDEL |
| PanNET7PT | CAMSAP1L1 | CCDS1404.1 | g.chr1:199085390>G | c.3319C>G | p.P1107A | MISSENSE |
| PanNET25PT | CCDC105 | CCDS12322.1 | g.chr19:14983104G>T | c.467G>T | p.R156L | MISSENSE |
| PanNET24PT | CCDC158 | CCDS43242.1 | g.chr4:77524825C>A | c.306G>T | p.E102D | MISSENSE |
| PanNET21PT | CD1A | CCDS1174.1 | g.chr1:156491632G>T | c.193G>T | p.V65F | MISSENSE |

FROM FIG. 5A

| Sample | Gene | CCDS | Genomic | cDNA | Protein | Type |
|---|---|---|---|---|---|---|
| PanNET10PT | CD1C | CCDS1175.1 | g.chr1:156528763G>A | c.594G>A | p.M198I | MISSENSE |
| PanNET7PT | CEP135 | CCDS33986.1 | g.chr4:56525306T>C | c.809T>C | p.I270T | MISSENSE |
| PanNET93PT | CILP | CCDS10203.1 | g.chr15:65276631C>T | c.3046G>A | p.D1016N | MISSENSE |
| PanNET23PT | COL1A1 | CCDS11561.1 | g.chr17:45629559C>T | c.731G>A | p.R244H | MISSENSE |
| PanNET31PT | CPNE8 | CCDS8733.1 | g.chr12:37508290C>G | c.1475G>C | p.R492T | MISSENSE |
| PanNET25PT | CRTAC1 | CCDS31266.1 | g.chr10:99657760C>A | c.850G>T | p.G284C | MISSENSE |
| PanNET7PT | CSPG4 | CCDS10284.1 | g.chr15:73762883C>T | c.4504G>A | p.G1502S | MISSENSE |
| PanNET3PT | CUX1 | CCDS5720.1 | g.chr7:101708039C>T | c.1663C>T | p.Q555X | NONSENSE |
| PanNET25PT | DAXX | CCDS4776.1 | g.chr6:33394939delT | c.1976delA | fs | INDEL |
| PanNET31PT | DAXX | CCDS4776.1 | g.chr6:33394935delC | c.1980delG | fs | INDEL |
| PanNET93PT | DAXX | CCDS4776.1 | g.chr6:33396641C>G | c.889G>C | p.A297P | MISSENSE |
| PanNET36PT | DDI1 | CCDS31680.1 | g.chr11:103412892G>A | c.232G>A | p.D78N | MISSENSE |
| PanNET7PT | DDIT4 | CCDS7315.1 | g.chr10:73704824G>T | c.571G>T | p.G191W | MISSENSE |
| PanNET31PT | DEFB118 | CCDS13177.1 | g.chr20:29424608C>A | c.346C>A | p.L116I | MISSENSE |
| PanNET10PT | DLC1 | CCDS5989.1 | g.chr8:12990585C>G | IVS 1G>C | SPLICE SITE | SPLICESITE |
| PanNET7PT | DNAJC5 | CCDS13546.1 | g.chr20:62031134G>A | c.133G>A | p.D45N | MISSENSE |
| PanNET36PT | DYNC1H1 | CCDS9956.1 | g.chr14:101519279C>A | c.1132C>A | p.L378M | MISSENSE |
| PanNET93PT | DZIP1L | CCDS3096.1 | g.chr3:139279113C>G | c.1340G>C | p.R447P | MISSENSE |
| PanNET24PT | EED | CCDS8273.1 | g.chr11:85657234G>A(hom) | c.949G>A(hom) | p.D317N | MISSENSE |
| PanNET21PT | EIF3D | CCDS13930.1 | g.chr22:35237727T>C | c.1402A>G | p.T468A | MISSENSE |
| PanNET23PT | ENOX1 | CCDS9389.1 | g.chr13:42828132C>T | c.746G>A | p.R249Q | MISSENSE |
| PanNET3PT | FGFR1A | CCDS933.1 | g.chr1:148029542G>A | c.970G>A | p.D324N | MISSENSE |
| PanNET23PT | FGF12 | CCDS3301.1 | g.chr3:193371021T>C | c.533A>G | p.N178S | MISSENSE |

FROM FIG. 5B

| | | | | |
|---|---|---|---|---|
| PanNET24PT | FRMD4A | CCDS7101.1 | g.chr10:13741461G>A(hom) | p.A645V | MISSENSE |
| PanNET31PT | FUT10 | CCDS8088.1 | g.chr8:33366460G>A | c.773C>T | p.P258S | MISSENSE |
| PanNET21PT | G6PC2 | CCDS2230.1 | g.chr2:169472367A>T | c.600A>T | p.Q200H | MISSENSE |
| PanNET31PT | GABRQ | CCDS14707.1 | g.chrX:151570711C>T | c.968C>T | p.S323F | MISSENSE |
| PanNET24PT | GLUD2 | CCDS14603.1 | g.chrX:120009460G>A | c.241G>A | p.V81M | MISSENSE |
| PanNET93PT | GPR112 | CCDS35409.1 | g.chrX:135238186G>A | c.4655G>A | p.C1552Y | MISSENSE |
| PanNET10PT | GPR81 | CCDS9236.1 | g.chr12:121780452G>A | c.388C>T | p.R130W | MISSENSE |
| PanNET10PT | GTF2IRD2B | CCDS34659.1 | g.chr7:74202815A>G | c.2626A>G | p.T876A | MISSENSE |
| PanNET31PT | GZMA | CCDS33965.1 | g.chr5:54441682G>C | c.704G>C | p.G235A | MISSENSE |
| PanNET93PT | HERC2P3 | ENST00000324413 | g.chr15:18918957C>C | c.1224C>G | p.S408R | MISSENSE |
| PanNET25PT | HIP1 | CCDS34669.1 | g.chr7:75022766T>C | c.1853A>G | p.D618G | MISSENSE |
| PanNET24PT | HIPK3 | CCDS7884.1 | g.chr11:33331571A>G | c.3529A>G | p.T1177A | MISSENSE |
| PanNET24PT | HIST1H2BD | CCDS4587.1 | g.chr6:26266492C>T | c.116C>T | p.S39L | MISSENSE |
| PanNET23PT | HS6ST1 | CCDS42748.1 | g.chr2:128742889G>A | c.553C>T | p.R185X | NONSENSE |
| PanNET31PT | HSD17B4 | CCDS4126.1 | g.chr5:118809525A>G | c.1588A>G | p.I530V | MISSENSE |
| PanNET31PT | IGBP1 | CCDS14396.1 | g.chrX:69283250G>T | c.526G>T | p.M175I | MISSENSE |
| PanNET24PT | IGFN1 | CCDS1409.1 | g.chr1:199462691G>A(hom) | c.2525G>A(hom) | p.G842E | MISSENSE |
| PanNET25PT | IL1RAPL1 | CCDS14218.1 | g.chrX:29863608C>T | c.1841C>T | p.T614M | MISSENSE |
| PanNET23PT | IL32 | CCDS32377.1 | g.chr16:3059299_3059300insG | c.509_510insG | fs | INDEL |
| PanNET23PT | INPP5B | CCDS41306.1 | g.chr1:38112360G>T | c.1843C>A | p.H615N | MISSENSE |
| PanNET3PT | IRS1 | CCDS2463.1 | g.chr2:227369663C>A(hom) | c.2036C>T(hom) | p.P679L | MISSENSE |
| PanNET93PT | ITGAX | CCDS10711.1 | g.chr16:31281451C>T | c.1235C>T | p.A412V | MISSENSE |
| PanNET93PT | KANK1 | CCDS34976.1 | g.chr9:702441G>C | c.1675G>C | p.V559L | MISSENSE |

FROM FIG. 5C

| Sample | Gene | CCDS | Genomic | c. | p. | Type |
|---|---|---|---|---|---|---|
| PanNET36PT | KAT2B | CCDS2634.1 | g.chr3:20088934C>T | c.409C>T | p.R137W | MISSENSE |
| PanNET23PT | KATNAL2 | CCDS32828.1 | g.chr18:42049860A>T | c.683A>T | p.K228M | MISSENSE |
| PanNET10PT | KCNC2 | CCDS9007.1 | g.chr12:73728331G>A | c.1649C>T | p.P550L | MISSENSE |
| PanNET25PT | KIAA0467 | CCDS30694.1 | g.chr1:43688893_43688897delTGAAG | c.1923_1927delTGAAG | fs | INDEL |
| PanNET10PT | LATS2 | CCDS9294.1 | g.chr13:20460280C>A | c.1639G>T | p.G547C | MISSENSE |
| PanNET23PT | LCN8 | CCDS35183.1 | g.chr9:138770846C>T | c.175G>A | p.E59K | MISSENSE |
| PanNET36PT | LGR5 | CCDS9000.1 | g.chr12:70248937C>T | c.1048C>T | p.Q350X | NONSENSE |
| PanNET10PT | LILRB5 | CCDS12865.1 | g.chr19:54446589G>A | c.1646C>T | p.P549L | MISSENSE |
| PanNET21PT | LPA | CCDS43523.1 | g.chr6:160927504G>C | c.4096C>G | p.P1366A | MISSENSE |
| PanNET10PT | LYPD3 | CCDS12620.1 | g.chr19:48661509G>T | c.55C>A | p.L19M | MISSENSE |
| PanNET10PT | MAMDC2 | CCDS8631.1 | g.chr9:71931041T>C | c.790T>C | p.Y264H | MISSENSE |
| PanNET10PT | MAP1A | CCDS42031.1 | g.chr15:41605959G>A | c.4996G>A | p.E1666K | MISSENSE |
| PanNET3PT | MAP3K10 | CCDS12549.1 | g.chr19:45402278C>T | c.910C>T | p.R304C | MISSENSE |
| PanNET26PT | MAP4 | CCDS3750.1 | g.chr3:47932748C>T | c.1573G>A | p.E525K | MISSENSE |
| PanNET3PT | MEN1 | CCDS8083.1 | g.chr11:64331709G>A(hom) | c.689C>T(hom) | p.G230V | MISSENSE |
| PanNET10PT | MEN1 | CCDS8083.1 | g.chr11:64334105_64334108delTCGT(hom) | c.50_53delACGA(hom) | fs | INDEL |
| PanNET23PT | MEN1 | CCDS8083.1 | g.chr11:64331233_64331234delAG(hom) | c.832_833delCT(hom) | fs | INDEL |
| PanNET31PT | MEN1 | CCDS8083.1 | g.chr11:64328587G>T | c.1643C>A | p.S548X | NONSENSE |
| PanNET93PT | MEN1 | CCDS8083.1 | g.chr11:64333906_64333909delAGAC | c.245_248delGTCT | fs | INDEL |
| PanNET21PT | MOCS1 | CCDS4845.1 | g.chr6:39982597T>A | c.1415A>T | p.E472V | MISSENSE |
| PanNET23PT | MRGPRX3 | CCDS7830.1 | g.chr11:18115377C>T(hom) | c.52C>T(hom) | p.R18C | MISSENSE |
| PanNET31PT | MYC | ENST00000259523 | g.chr8:128201111G>A | c.421G>A | p.A141T | MISSENSE |
| PanNET93PT | MYH6 | CCDS9600.1 | g.chr14:22937812C>T | c.1856C>A | p.A619D | MISSENSE |

FROM FIG. 5D

| Sample | Gene | Accession | Genomic | cDNA | Protein | Type |
|---|---|---|---|---|---|---|
| PanNET36PT | NAA25 | CCDS9159.1 | g.chr12:111015323T>A | c.59A>T | p.D20V | MISSENSE |
| PanNET25PT | NF1 | CCDS42292.1 | g.chr17:26687564G>A | c.6094G>A | p.A2032T | MISSENSE |
| PanNET7PT | NID2 | CCDS9706.1 | g.chr14:51575327G>C | c.2145C>G | p.H715Q | MISSENSE |
| PanNET23PT | N/NL | CCDS33452.1 | g.chr20:25404793C>G | c.3134G>C | p.G1045A | MISSENSE |
| PanNET10PT | NM_170692 | NM_170692 | g.chr1:176330297G>A | c.47G>A | p.W16X | NONSENSE |
| PanNET93PT | NSG00000019695 | CCDS32450.1 | g.chr16:54417626C>G | c.343G>C | p.E115Q | MISSENSE |
| PanNET25PT | NSG00000018529 | CCDS32673.1 | g.chr17:41278807C>T | c.755C>T | p.T252M | MISSENSE |
| PanNET23PT | NSG00000022189 | CCDS12848.1 | g.chr19:57230244T>C | c.500A>G | p.H167R | MISSENSE |
| PanNET10PT | MI0003151 | MI0003151 | g.chr19:58890336A>C | c.58A>C | p.I20L | MISSENSE |
| PanNET31PT | NM_004742 | NM_004742 | g.chr3:6532188C>G | c.3756C>G | p.P1252R | MISSENSE |
| PanNET24PT | NSG00000020421 | CCDS4774.1 | g.chr6:33372847C>G | c.180G>C | p.E60D | MISSENSE |
| PanNET23PT | NSG00000011670 | CCDS30592.1 | g.chr1:12862491A>C | c.898T>G | p.F300V | MISSENSE |
| PanNET23PT | NSG00000012338 | CCDS8932.1 | g.chr2:55890166G>A | c.12527G>A | p.R4176Q | MISSENSE |
| PanNET23PT | NSG00000019845 | CCDS4735.1 | g.chr6:32115939_32115940insT | c.917_918insT | fs | INDEL |
| PanNET23PT | OD21 | CCDS14609.1 | g.chrX:123342209C>T(hom) | c.8036G>A(hom) | p.G2679E | MISSENSE |
| PanNET7PT | OXCT2 | CCDS445.1 | g.chr1:40008388A>C | c.1127T>G | p.F376C | MISSENSE |
| PanNET10PT | PAF1 | CCDS12533.1 | g.chr19:44568755C>T | c.1312G>A | p.E438K | MISSENSE |
| PanNET3PT | PDE8A | CCDS10336.1 | g.chr15:83480854C>G(hom) | c.2339C>G(hom) | p.S780C | MISSENSE |
| PanNET3PT | PDP1 | CCDS6259.1 | g.chr8:95004154G>C(hom) | c.691G>C(hom) | p.D231H | MISSENSE |
| PanNET25PT | PGLYRP3 | CCDS1035.1 | g.chr1:151541551G>A | c.686C>T | p.S229F | MISSENSE |
| PanNET10PT | PIK3CA | CCDS43171.1 | g.chr3:180418785G>A | c.1633G>A | p.E545K | MISSENSE |
| PanNET31PT | PLAC1 | CCDS14642.1 | g.chrX:133528078A>T | c.301T>A | p.S101T | MISSENSE |
| PanNET23PT | PLEKHG4 | CCDS32466.1 | g.chr16:65377797C>A | c.349C>A | p.Q117K | MISSENSE |

FROM FIG. 5E

| Sample | Gene | CCDS | Genomic | Coding | Protein | Type |
|---|---|---|---|---|---|---|
| PanNET23PT | PNRC2 | CCDS246.1 | g.chr1:24160871C>T | c.337C>T | p.H113Y | MISSENSE |
| PanNET3PT | POLR2J | CCDS5724.1 | g.chr7:101905259_101906261delCTT | c.52_54delAA | fs | INDEL |
| PanNET93PT | PPP1R3A | CCDS5759.1 | g.chr7:113003329C>G | IVS3+1G>C | SPLICE SITE | SPLICESITE |
| PanNET25PT | PRKCB | CCDS10619.1 | g.chr16:24133624G>A | c.2008G>A | p.E670K | MISSENSE |
| PanNET3PT | PRKRIR | CCDS8243.1 | g.chr11:75739608G>C | c.2234C>G | p.I745R | MISSENSE |
| PanNET25PT | PRPF4 | CCDS6791.1 | g.chr9:115081210G>A | c.373G>A | p.G125S | MISSENSE |
| PanNET3PT | PRRX2 | CCDS6926.1 | g.chr9:131524367T>C | c.677T>C | p.V226A | MISSENSE |
| PanNET10PT | PTEN | CCDS31238.1 | g.chr10:89707693delG | c.738delG | fs | INDEL |
| PanNET31PT | PTEN | CCDS31238.1 | g.chr10:89682819T>G | c.323T>G | p.L108R | MISSENSE |
| PanNET7PT | PTPRC | CCDS1397.1 | g.chr1:198932643A>C | c.274A>C | p.S92R | MISSENSE |
| PanNET10PT | RSPH10B | CCDS34598.1 | g.chr7:5941281C>T | c.2035G>A | p.A679T | MISSENSE |
| PanNET24PT | RTTN | CCDS42443.1 | g.chr18:65986186T>C | c.1751A>G | p.Y584C | MISSENSE |
| PanNET21PT | SAMSN1 | CCDS42906.1 | g.chr21:14794733C>G | c.756G>C | p.R252S | MISSENSE |
| PanNET23PT | SERTAD4 | CCDS1494.1 | g.chr1:208482159G>T | c.925G>T | p.E309X | NONSENSE |
| PanNET24PT | SLC1A4 | CCDS1879.1 | g.chr2:65070658T>C(hom) | c.377T>C(hom) | p.L126P | MISSENSE |
| PanNET3PT | SLC25A23 | CCDS32882.1 | g.chr19:6405347A>C | c.782T>G | p.M261R | MISSENSE |
| PanNET31PT | SLC26A10 | CCDS8947.1 | g.chr12:56296444C>T | c.1528C>T | p.Q510X | NONSENSE |
| PanNET24PT | SLC35E2 | CCDS33.1 | g.chr1:1656027C>T | c.694G>A | p.V232I | MISSENSE |
| PanNET3PT | SLC6A14 | CCDS14570.1 | g.chrX:115488967delC | c.637delC | fs | INDEL |
| PanNET10PT | SLC6A8 | CCDS14726.1 | g.chrX:152613767_152613768insG(hom) | c.1812_1813insG(hom) | fs | INDEL |
| PanNET93PT | SMG7 | CCDS1335.1 | g.chr1:181781019A>T | c.2319A>T | p.K773N | MISSENSE |
| PanNET23PT | SP8 | CCDS43555.1 | g.chr7:20791689C>A | c.92C>T | p.S31I | MISSENSE |
| PanNET24PT | SSB | CCDS2237.1 | g.chr2:170373276_170373280delAAAAT | c.593_597delAAAAT | fs | INDEL |

FROM FIG. 5F

| | | | | | |
|---|---|---|---|---|---|
| PanNET93PT | STON2 | CCDS9875.1 | g.chr14:80813088C>T | c.2320G>A | MISSENSE |
| PanNET21PT | SULT2A1 | CCDS12707.1 | g.chr19:53066328C>A | c.754G>T | MISSENSE |
| PanNET10PT | SUPT3H | CCDS12536.1 | g.chr19:44640153A>C | IVS2-2A>C | SPLICESITE |
| PanNET26PT | TATDN2 | CCDS33898.1 | g.chr3:10276849C>T | c.443C>T | MISSENSE |
| PanNET24PT | TDRKH | CCDS41394.1 | g.chr1:115001921 9C>G(hom) | c.253C>G(hom) | MISSENSE |
| PanNET29PT | TFCP2L1 | CCDS2134.1 | g.chr2:121711722C>G | c.950G>C | MISSENSE |
| PanNET24PT | THAP9 | CCDS3598.1 | g.chr4:84057916_84057917insT | c.1527_1528insT | INDEL |
| PanNET31PT | TMC4 | CCDS12882.1 | g.chr19:59357735G>A | c.1601C>T | MISSENSE |
| PanNET24PT | TRPM3 | CCDS43835.1 | g.chr9:72341936C>T | c.3877G>A | MISSENSE |
| PanNET31PT | TSC2 | CCDS10458.1 | g.chr16:2074957G>A | c.4498G>A | MISSENSE |
| PanNET93PT | TSC2 | CCDS10458.1 | g.chr16:2038643C>A | c.26C>A | NONSENSE |
| PanNET10PT | TTC15 | CCDS1652.1 | g.chr2:3407407C>G | c.1383C>G | NONSENSE |
| PanNET10PT | TTC21B | CCDS33315.1 | g.chr2:166477283T>C | c.2309A>G | MISSENSE |
| PanNET93PT | TWSG1 | CCDS11844.1 | g.chr18:9336368G>A | c.314G>A | MISSENSE |
| PanNET36PT | TXNDC2 | CCDS42414.1 | g.chr18:9976865A>G | c.389A>G | MISSENSE |
| PanNET3PT | UACA | CCDS10235.1 | g.chr15:68709900T>C | c.371A>G | MISSENSE |
| PanNET21PT | UNC5C | CCDS3643.1 | g.chr4:96360288G>C | c.1171C>G | MISSENSE |
| PanNET93PT | UNC5D | CCDS60993.1 | g.chr8:35663562G>A | c.952G>A | MISSENSE |
| PanNET10PT | USP29 | CCDS33124.1 | g.chr19:62333513G>T | c.1638G>T | MISSENSE |
| PanNET3PT | VPS13A | CCDS6655.1 | g.chr9:79080958G>A | IVS26+1G>A | SPLICESITE |
| PanNET21PT | ZDHHC11 | CCDS3857.1 | g.chr5:893661A>G | c.733T>C | MISSENSE |
| PanNET23PT | ZEB2 | CCDS2186.1 | g.chr2:144875238C>G(hom) | c.914G>C(hom) | MISSENSE |
| PanNET93PT | ZNF229 | CCDS42574.1 | g.chr19:49626423T>A | c.373A>T | MISSENSE |

FROM FIG. 5G

| | | | | |
|---|---|---|---|---|
| PanNET21PT | ZNF93 | CCDS32973.1 | g.chr19:19905861A>C | c.1097A>C | p.K366T | MISSENSE |
| PanNET21PT | ZNF543 | CCDS33130.1 | g.chr19:62531154A>T | c.512A>T | p.Q171L | MISSENSE |
| PanNET7PT | ZNF544 | CCDS12973.1 | g.chr19:63464732_63464735delAGAA | c.948_951delAGAA | fs | INDEL |
| PanNET31PT | ZNF557 | CCDS42485.1 | g.chr19:7034310A>G | c.848A>G | p.K283R | MISSENSE |
| PanNET31PT | ZNF678 | CCDS1560.1 | g.chr1:225909443_225909446delAGAA(hom) | c.365_368delAGAA(hom) | fs | INDEL |
| PanNET36PT | ZNF787 | CCDS42634.1 | g.chr19:61306335T>A | c.64>T | p.S22C | MISSENSE |
| PanNET7PT | ZZEF1 | CCDS11043.1 | g.chr17:3973968C>T | c.481G>A | p.A161T | MISSENSE |

*ALL COORDINATES REFER TO THE HUMAN REFERENCE GENOME hg18 RELEASE (NCBI 36.1, MARCH 2006).

FIG. 5H

Fig. 6 table S3. Comparison of commonly mutated genes in PanNETs and PDAC.

| Genes[a] | PanNET | PDAC[b] |
|---|---|---|
| MEN1 | 44% | 0% |
| DAXX, ATRX | 43% | 0% |
| MTOR | 15% | 0.80% |
| TP53 | 3% | 85% |
| KRAS | 0% | 100% |
| CDKN2A | 0% | 25% |
| TGFBR1, SMAD3, SMAD4 | 0% | 38% |

[a] Includes point mutations and indels.
[b] Data from Jones et al., Science 321, 1801 (2008).

Fig. 7 table S4. Comparison of somatic point mutation spectra in PanNETs and PaCa.

| Base pair change | PanNET | | PDAC[a] | |
|---|---|---|---|---|
| | % | number | % | number |
| C:G to T:A | 42.2% | 62 | 53.8% | 798 |
| C:G to G:C | 17.7% | 26 | 9.6% | 142 |
| C:G to A:T | 15.0% | 22 | 16.6% | 246 |
| T:A to C:G | 12.9% | 19 | 9.6% | 142 |
| T:A to G:C | 5.4% | 8 | 5.3% | 79 |
| T:A to A:T | 6.9% | 10 | 5.2% | 77 |

*Data from Jones *et al*., *Science* 321, 1801 (2008).
The mutation spectra of PanNet and PDAC are significantly different, P= 0.04.

Fig. 8 table S5. Immunohistochemistry (IHC) of ATRX and DAXX

| PanNET # | ATRX IHC | DAXX IHC | Mutation |
|---|---|---|---|
| 5 | NEG | POS | ATRX |
| 6 | POS | POS | WT |
| 9 | POS | POS | WT |
| 13 | NEG | POS | ATRX |
| 21 | POS | POS | WT |
| 24 | POS | POS | WT |
| 25 | POS | HET | DAXX |
| 27 | NEG | POS | ATRX |
| 29 | POS | POS | WT |
| 31 | POS | POS | DAXX |
| 35 | NEG | POS | ATRX |
| 36 | POS | POS | WT |
| 44 | POS | NEG | DAXX |
| 56 | POS | NEG | DAXX |
| 59 | POS | POS | ATRX |
| 61 | NEG | POS | WT |
| 63 | POS | POS | WT |
| 64 | HET | POS | WT |
| 66 | POS | POS | WT |
| 76 | POS | POS | WT |
| 77 | POS | NEG | DAXX |
| 78 | POS | POS | ATRX |
| 79 | POS | POS | WT |
| 80 | POS | NEG | WT |
| 83 | POS | POS | WT |
| 84 | POS | POS | DAXX |
| 85 | NEG | POS | ATRX |
| 87 | POS | POS | DAXX |
| 93 | POS | NEG | DAXX |
| 104 | POS | NEG | DAXX |
| 121 | POS | POS | WT |
| 125 | NEG | POS | WT |
| 133 | POS | NEG | DAXX |

NEG = Uniformly negative labeling of tumor cells
POS = Unifromly positive labeling of tumor cells
HET = Heterogeneous labeling of tumor cells
WT = Wild type
In the two cases with negative staining but without a mutation, an undetected mutation or silencing may have occurred.
In the five cases with a mutation that still stained uniformly for both ATRX and DAXX protein, the mutations were either missense, heterozygous or affected residues C-terminal to those recognized by the antibody.

Fig. 9
table S6 Patient Characteristics.

|  | All Patients (n=68) |
|---|---|
| Age - Median (Range in years) | 54 (32-92) |
| Gender - No (%) | |
| Male | 36 (53) |
| Female | 32 (47) |
| Race - Number (%) | |
| African American | 3 (4) |
| Caucasian | 58 (85) |
| Asian | 2 (3) |
| Hispanic | 1 (2) |
| Other | 4 (6) |
| Liver Metastases - Number (%) | |
| Present | 28 (41) |
| Absent | 40 (59) |
| Surgical Procedure - Number (%) | |
| Partial or Total Pancreatectomy | 49 (72) |
| Partial or Total Pancreatectomy and Liver resection | 9 (13) |
| Liver resection only | 10 (15) |
| Mutations in PTEN/PIK3CA/MTOR Pathway - Number (%) | |
| Present | 7 (10) |
| Absent | 61 (90) |
| Mutations in MEN1 Pathway - Number (%) | |
| Present | 32 (47) |
| Absent | 36 (53) |
| Mutations in DAXX/ATRX Pathway - Number (%) | |
| Present | 29 (43) |
| Absent | 39 (57) |
| Median Survival (years) | 12.3 |
| Primary Tumor size (cm) | 4.85 |
| % Ki67 - Number (%) | |
| 0-2 | 18(26) |
| >2-20 | 38(56) |

| | >20 | 4(6) |
| --- | --- | --- |
| | Not Done | 8(12) |
| Mitoses per ten high power fields - Number (%) | | |
| | 0-2% | 46 (68) |
| | 2-20% | 15 (22) |
| | >20% | 1 (1) |
| | Not Done | 6 (9) |

Fig. 9 - continued

TABLE S7. SURVIVAL ESTIMATES

| | | n* | MEDIAN SURVIVAL (IN YEARS) | HAZARD RATIO | 95% CI | p-VALUE | 5-YEAR OS | 10 YEAR OS |
|---|---|---|---|---|---|---|---|---|
| ALL PATIENTS | | 66 | 12.3 | | | | 81% | 64% |
| EXTENT OF DISEASE | LOCALIZED | 39 | NOT-REACHED | 3.0 | 1.1 TO 7.7 | 0.03 | 88% | 73% |
| | METASTATIC | 27 | 11.8 | | | | 72% | 52% |
| PIK3CA/PTEN/MTOR PATHWAY MUTATIONS | PRESENT | 7 | NOT-REACHED | 1.0 | 0.13 TO 7.9 | 0.99 | 80% | NOT-REACHED |
| | ABSENT | 59 | 12.3 | | | | 82% | 64% |
| MEN1 MUTATIONS (ALL) | PRESENT | 31 | 12.3 | 0.55 | 0.22 TO 1.4 | 0.20 | 92% | 77% |
| | ABSENT | 36 | NOT-REACHED | | | | 81% | 54% |
| MEN1 MUTATIONS (METASTATIC DISEASE) | PRESENT | 16 | 11.8 | 0.28 | 0.071 TO 1.1 | 0.07 | 84% | 72% |
| | ABSENT | 11 | 5.1 | | | | 71% | 28% |
| DAXX/ATRX PATHWAY MUTATIONS (ALL) | PRESENT | 27 | 14.1 | 0.44 | 0.18 TO 1.1 | 0.08 | 96% | 80% |
| | ABSENT | 39 | 12.3 | | | | 72% | 54% |
| DAXX/ATRX PATHWAY MUTATIONS (METASTATIC DISEASE) | PRESENT | 15 | 11.8 | 0.22 | 0.059 TO 0.84 | 0.03 | 92% | 50% |
| | ABSENT | 12 | 5.5 | | | | 79% | 25% |
| DAXX/ATRX AND MEN1 PATHWAY MUTATIONS (ALL) | BOTH PATHWAYS MUTATED | 18 | 14.1 | 0.37 | 0.12 TO 1.1 | 0.08 | 100% | 86% |
| | NEITHER PATHWAY MUTATED | 26 | NOT-REACHED | | | | 52% | 52% |
| DAXX/ATRX AND MEN1 PATHWAY MUTATIONS (METASTATIC DISEASE) | BOTH PATHWAYS MUTATED | 10 | 13.0 | 0.067 | 0.0089 TO 0.51 | 0.01 | 100% | 100% |
| | NEITHER PATHWAY MUTATED | 6 | 5.15 | | | | 50% | 33% |

* TWO PATIENTS WITH PERIOPERATIVE DEATH WERE EXCLUDED

FIG. 10

TABLE S8. PRIMERS USED FOR PCR AMPLIFICATION AND SEQUENCING

| GENE SYMBOL | TRANSCRIPT IDs | CODING EXON NUMBER | GENOMIC REGION OF INTEREST* | M13 PCR PRIMER SEQUENCE† | PCR PRIMER SEQUENCE |
|---|---|---|---|---|---|
| ATRX | ENST00000373344 | 1 | chrX:76650481_76650767 | ATGGTCCTGTGAATGCCATC | GGCATTTAAGGGGACGAAAC |
| ATRX | ENST00000373344 | 2 | chrX:76662918_76663054 | ACCTTGGGAAATCCCGAATA | CAATGACTATCCATCCCTCCA |
| ATRX | ENST00000373344 | 3 | chrX:76662918_76663636 | GTTGGCAAATGGAAGGATTC | AGTAGGGGGTGGAGGGTACA |
| ATRX | ENST00000373344 | 4 | chrX:76664393_76684526 | GGGTGAAAGGGTGTTTTGTT | GCATAGGGAACCCTCAACAA |
| ATRX | ENST00000373344 | 5 | chrX:76665382_76665539 | GGTTTAGTTTCTAGTACAGTTGACCA | GGGGAATGTGTTCCTAAAACC |
| ATRX | ENST00000373344 | 6 | chrX:76699574_76699776 | GCAAAATTGCTGATGAGTTTTT | CATTTATTATCCTTGAAAATTCTGA |
| ATRX | ENST00000373344 | 7 | chrX:76700792_76700977 | AAGAAATGAATTCTCTGAACTCTTGA | CCAACTTTGTTTCCCTCTCTG |
| ATRX | ENST00000373344 | 8 | chrX:76716367_76716483 | TGATGAGCAAGGTGGAAAATC | TGACACTGTTTTGCAACCTGA |
| ATRX | ENST00000373344 | 9 | chrX:76731956_76732070 | AAATCCTGCTGGGATTCTTTT | GGGTAGTTTTGTTTCTTTTGTTGC |
| ATRX | ENST00000373344 | 10 | chrX:76735818_76735979 | CCCCATGGGTAGGTCTTTT | TTGCTTGTATTGGCCTAGCA |
| ATRX | ENST00000373344 | 11_12 | chrX:76741532_76741949 | TCAGTCCTTCCTCAGCTCGT | TCCATGATAAAGGCAACATTCA |
| ATRX | ENST00000373344 | 13 | chrX:76742685_76742693 | GCTTCTCTACACTGCCAAAAGTG | TTCTGCTTCCAATACGATGCTTT |
| ATRX | ENST00000373344 | 14 | chrX:76758733_76758858 | TTGTGGGTTTAGAAAGGGTAAA | TGCAAAACTGAAAAAGAACAACA |
| ATRX | ENST00000373344 | 15 | chrX:76760926_76761109 | TGAGCATTTCATTGGGGAAT | TGAAAGAGCGGGAAAGAAAA |
| ATRX | ENST00000373344 | 16 | chrX:76762515_76762660 | TTAACCAAATACGGGAGCAGA | TTTCACGCAGACTAAGATGAACC |
| ATRX | ENST00000373344 | 17 | chrX:76775347_76775532 | GGCAAGAGGGGATTAAAAGATGA | TGGCGACATTAAGGGTGATT |
| ATRX | ENST00000373344 | 18 | chrX:76775706_76775860 | TTGGAAATTCTGGCCGGTTA | TTCCCACTCGAAATATGCATCAC |
| ATRX | ENST00000373344 | 19 | chrX:76776737_76776854 | TCTTCAGCCCCTACGACTGT | GAAGGAAAGTCCCCCTGTTC |
| ATRX | ENST00000373344 | 20 | chrX:76778058_76778207 | CAATTGGATTTGTGGTGTGG | CCACCCACTCACCAATTTA |
| ATRX | ENST00000373344 | 21 | chrX:76794256_76794503 | CCACCTTTTCCTGCTGTGTT | CATTAATAGAAATAAATTAAGG |
| ATRX | ENST00000373344 | 22 | chrX:76796240_76796350 | AATGAAGGGTTAGGCTGCTG | TGGAACAGAGAGGTAACAGCA |

FROM FIG. 11A

| | | | | |
|---|---|---|---|---|
| ATRX | ENST00000373344 | 23 | chrX:76799702_76799803 | TGCTCTGTTTAATGTCGAGTCA | TGAAGGCATGGTCATTCAGA |
| ATRX | ENST00000373344 | 24 | chrX:76805523_76805707 | CAGCTTCCCAAAGTGCTAGG | CGAGGCATTTTAAAGGCTGA |
| ATRX | ENST00000373344 | 25 | chrX:76805786_76806927 | TCTATTGGCACATTTATTCT | TTGCCTCCCAAAGTCCTGAGATT |
| ATRX | ENST00000373344 | 26 | chrX:76818373_76818453 | TTGGAGTCCAGAGTTTAGACC | AACTTGAGGAAGACTGTGACGGA |
| ATRX | ENST00000373344 | 27 | chrX:76820192_76826745 | CCAATGCAAGATGAGGCTTC | GAGTAAGCAGATGACCTAAATTACCAC |
| ATRX | ENST00000373344 | 27 | chrX:76825762_76826379 | CTTGTTCAGTTCCACTGCTGCCAT | CCTGTCTCGGCTCTGTAACCTACT |
| ATRX | ENST00000373344 | 27 | chrX:76825202_76825912 | CCGGTCGTGAACATAAGAAATCTG | AACTGTGACTCATCCTGCTCACCT |
| ATRX | ENST00000373344 | 27 | chrX:76825281 | GGATAAGCGTAATTCTTCTGACAGTGC | AGCACTTGCTTGCTTGCTTCTTAGG |
| ATRX | ENST00000373344 | 27 | chrX:76824800 | AGGAATGGATAATAATCAAGGGCACA | TCCTTTCCCTGTTGACTTCTCAGC |
| ATRX | ENST00000373344 | 27 | chrX:76824202_76824348 | TGAATCTTCATCTGATGCACTGA | TTTCTGTTCATCGCTGCTGCCCTC |
| ATRX | ENST00000373344 | 27 | chrX:76823754_76824348 | CATCTGATGCTGAGGAAAGTTCTG | GAGATCCCTGATACTGAATACTAGC |
| ATRX | ENST00000373344 | 27 | chrX:76823668_76823916 | CACACCAGTGTCCTGGAGATT | AGGAAACACTGAATGTTAGCTCATCT |
| ATRX | ENST00000373344 | 28 | chrX:76827083_76827158 | TGCCAAGGTTGTCATGTCTTAG | GAAGTCTTCCAAGGCAGATACCA |
| ATRX | ENST00000373344 | 29 | chrX:76830963_76831080 | CCAGCAATGTGGCTTTATCTGAACTG | TCACTGTATTTACCTCCGCGT |
| ATRX | ENST00000373344 | 30 | chrX:76835969_76836081 | TTCCTTGTTGAGACCCACTGCTCA | GCCATGTTTGGTCGTTGTACATAGT |
| ATRX | ENST00000373344 | 31 | chrX:76838717_76838852 | GCTAATTGTAGGGATGCCGTTTCG | CTCAGAATAGTGGTTGACATGAGTTCAG |
| ATRX | ENST00000373344 | 32 | chrX:76839723_76839783 | AGTGTCGAGAATGGGTTTGTGGAGT | TGGGTATCAGTAGCCTTCGACACA |
| ATRX | ENST00000373344 | 33 | chrX:76840714_76840777 | GGGCTTCTATAAAGCTTGCTAATCTGTC | ACACCCACAACTGTAACATTTCCC |
| ATRX | ENST00000373344 | 34 | chrX:76859260_76859380 | TGTGCTTGGAGGAGGTAGGCAAT | TAAGCAACACAGGCCTAACCCA |
| ATRX | ENST00000373344 | 35 | chrX:76928120_76928147 | GTGCCACATCCTCGTCTTCC | GGGACAGCTAATGCCAATCTG |
| DAXX | ENST00000266000 | 1 | chr6:33394494_33394561 | AAGAGACAGGATGTGGCACG | GTCTGCTGGGAGAGACTGGAC |
| DAXX | ENST00000266000 | 2 | chr6:33394748_33394978 | TCTCCCAGAGACTCAGTTCC | CAAAGGACGCATAGTGTCACC |
| DAXX | ENST00000266000 | 3 | chr6:33395131_33395366 | CAAGGGAACATTCTCCTCACC | CGCCTCCATTGAAGGAAGTAG |
| DAXX | ENST00000266000 | 3 | chr6:33395367_33395613 | GAGTCCAGGTTGACTGATGGG | GAAAGGTTTCAAACAGGTGGC |
| DAXX | ENST00000266000 | 4 | chr6:33395762_33395983 | ATGTCAGGTATGAGGCGGATG | CATCAGTCAACCTGGACTCCC |
| DAXX | ENST00000266000 | 5 | chr6:33396131_33396350 | | |

FROM FIG. 11C

| Gene | Transcript | # | Location | Seq1 | Seq2 |
|---|---|---|---|---|---|
| PIK3CA | ENST00000263967 | 13 | chr3:180421464_180421643 | GGCCACCTTCTATGTTCGAA | CAAGAAGCATAGGCGTGTGTC |
| PIK3CA | ENST00000263967 | 14 | chr3:180424559_180424673 | TTTGAGGGTAGGGAGAATGAGAGA | TCTGAGTGTTGCTGCTCTGTG |
| PIK3CA | ENST00000263967 | 15 | chr3:180425178_180425307 | TCTGTTACCATAGGATAAGAAATGGA | GCTAAATTCATGCATCATAAGCTC |
| PIK3CA | ENST00000263967 | 16 | chr3:180426440_180426526 | CATGTGATGGCGTGATCC | GGTGACACTCCAGAGGCAGTAG |
| PIK3CA | ENST00000263967 | 17 | chr3:180429750_180429928 | GGAAAGGCAGTAAGGTCATGC | GAGGAATACACAAACACCGACAG |
| PIK3CA | ENST00000263967 | 18 | chr3:180430482_180430607 | TAAATGGAAACTTGCACCTG | AAACAAATGGCACAGTTCTC |
| PIK3CA | ENST00000263967 | 19 | chr3:180430703_180430862 | TACCCAGGCTGGTTTCAATTC | TGGTGAAAGACGATGCACAAG |
| PIK3CA | ENST00000263967 | 20 | chr3:180434572_180434650 | GACATTTGAGCAAAGACCTGAAG | TGGATTGTGCAATTCCTATGC |
| PTEN | ENST00000371953 | 1 | chr10:89614203_89614289 | TCCGTCTAGCCAAACACACC | TTTCCATCCTGCAGAAGAAGC |
| PTEN | ENST00000371953 | 2 | chr10:89643758_89643850 | TCTGTGATGTGATAAACGTGAGTTTC | CCCTGAAGTCCATTAGGTACGG |
| PTEN | ENST00000371953 | 3 | chr10:89675246_89675298 | CATGATTACTACTCTAAACCCATAGAAGG | TCAAATATGGCTAGATGCCA |
| PTEN | ENST00000371953 | 4 | chr10:89680779_89680830 | GACCAACTGCCTCAAATAGTAGG | ATAAAGATTCAGGCAATGTTTGTTAG |
| PTEN | ENST00000371953 | 5 | chr10:89682746_89682992 | TTTACTTGTCAATTACACCTCAATAAA | TGCAACATTTCTAAAGTTACCTACTTG |
| PTEN | ENST00000371953 | 6 | chr10:89701851_89702000 | TTTGGCTTCTTTAGCCCAATG | AATGGCTACGACCCAGTACC |
| PTEN | ENST00000371953 | 7 | chr10:89707586_89707760 | TGCAGATACAGAATCCATATTTCG | AATGTCTCACCAATGCCAGAG |
| PTEN | ENST00000371953 | 8 | chr10:89710627_89710859 | TGTCAAGCAAGTTCTTCATCAGC | TGCAACAGATAACTCAGATTGCC |
| PTEN | ENST00000371953 | 9 | chr10:89715020_89715213 | AAAGATCATGTTTGTTACAGTGCTTAAA | TGACACAATGTCCTATTGCCA |
| TP53 | ENST00000269305 | 1 | chr17:7513648_7513737 | CCATCTTGATTTGAATTCCCG | ATTGCAAGCAAGGGTTCAAAG |
| TP53 | ENST00000269305 | 2 | chr17:7514648_7514762 | ACCTGCCTTTGACCATGAAG | ATTGACACATTGCACTCCC |
| TP53 | ENST00000359597 | 1 | chr17:7517346_7517386 | AGTTTATCAGGAAGTAACACCATCG | CAAAGACAATGGCTCCTGGTT |
| TP53 | ENST00000269305 | 3 | chr17:7517574_7517655 | GGAGCACTAAGGCAGGTAAGC | TTGTCTTTGAGGCATCACTGC |
| TP53 | ENST00000269305 | 4 | chr17:7517740_7517884 | TTGGCAGTGCTAGGAAAGAG | GTTGGGAGTAGATGGAGCCTG |
| TP53 | ENST00000269305 | 5 | chr17:7518220_7518337 | AGAATACGGTAAGAGGTGGGC | CATCCTGCTAACGGTGAAAC |
| TP53 | ENST00000269305 | 6 | chr17:7518899_7519018 | CTGCTCAGATACGGATGGTG | AGGCCCTTAGCCTCTGTAAGC |
| TP53 | ENST00000269305 | 7 | chr17:7519092_7519283 | GGGCCAGACCTAAGAGCAATC | AAGCTCCTGAGGTGTAGACGC |
| TP53 | ENST00000269305 | 8 | chr17:7520033_7520319 | GAGGAATCCCAAAGTTCAAAC | ACGTTCTGGTAAGGACAAGGG |
| TP53 | ENST00000269305 | 9 | chr17:7520421_7520450 | CAGTCAGATCCTAGCGTCGAG | AAATCATCCATTGCTTGCCCTTAC |
| TP53 | ENST00000269305 | 10 | chr17:7520560_7520641 | AGGGTTGGAAGTGTCTCATGC | AGCCCAACCCTTGTCCTTAC |
| TSC2 | ENST00000219476 | 1 | chr16:2038614_2038759 | GTGTGGGAGGAGGAAAGGTTATGC | GAACCTGGTGCAAGACCAAAC |

FROM FIG. 11D

| | | | | |
|---|---|---|---|---|
| TSC2 | ENST00000219476 | 2 | chr16:2040398_2040492 | TTAGGTGGTTTGTGACTTGCAG | GTGAGCCAAGATTGTGCCAG |
| TSC2 | ENST00000219476 | 3 | chr16:2043340_2043458 | AGATACGAGCTTTGGAGGTGG | ACCTCATGACCACCAGGAGACC |
| TSC2 | ENST00000219476 | 4 | chr16:2044294_2044446 | CTTCAGGGACTTCTTGGCAG | ACTCACAGTCAGCAGGTCTGG |
| TSC2 | ENST00000219476 | 5 | chr16:2044900_2045525 | TGGTGGTTTCAACTTATTCACTG | ATCCTAGTGTCCGTGCGTAGC |
| TSC2 | ENST00000219476 | 6 | chr16:2046194_2046250 | ACCTGAGTGCTTGTTGGGTG | TGAGGCTCAGAGAGACCGAG |
| TSC2 | ENST00000219476 | 7 | chr16:2046642_2046775 | CCCAAGAATCAGAGAACCATTC | ATGACAGCATCAATGACCCAC |
| TSC2 | ENST00000219476 | 8 | chr16:2047103_2047184 | TCTGTCTTTGGGAGGAGATGG | TCTCTAAGCCAGTGTGTGCTTG |
| TSC2 | ENST00000219476 | 9 | chr16:2048745_2048879 | GAAAGGCCTAGAAATGCCACC | GTTACTGCTGGCCTCTGTTCC |
| TSC2 | ENST00000219476 | 10 | chr16:2050668_2050819 | GAACACGGTTCTGCCAGTCTC | CCTGATAAACGTGTGTGGTGGG |
| TSC2 | ENST00000219476 | 11 | chr16:2051869_2052014 | GAGAGGGCTGAGGGTGTCTC | GCTCAGAAAGCTGCACTTCAC |
| TSC2 | ENST00000219476 | 12 | chr16:2052495_2052606 | CTCTGACAGCAAACCAGCCTC | ACTGGAAAGCAAGCTAGGACC |
| TSC2 | ENST00000219476 | 13 | chr16:2052970_2053059 | GTGCACAACAGAGACAGCCC | AGGTGCTAGCTTGCTTTCCAG |
| TSC2 | ENST00000219476 | 14 | chr16:2054270_2054433 | TGAGGAATTGGAAGTGTCACG | ACTCGAAGAGGAGGACAGAGG |
| TSC2 | ENST00000219476 | 15 | chr16:2055517_2055604 | GACTCCAACACAACGCAGATG | TGACCTGAGATTGTGCCACC |
| TSC2 | ENST00000219476 | 16 | chr16:2060454_2060584 | GACTGCAGGGAGAGGGAAG | GAGAGAGTCCTGGTGGTCCTG |
| TSC2 | ENST00000219476 | 17 | chr16:2061508_2061622 | TTCTGAGTGCCTGTGGTGC | ACAGACTTGGCTCTTCCCAAC |
| TSC2 | ENST00000219476 | 18 | chr16:2061782_2061940 | CTATGGAGCCCTGTTCTCAGC | GTTGGGAAGAGCCAAGTCTG |
| TSC2 | ENST00000219476 | 19 | chr16:2062239_2062369 | GCTGAGAACAGGGCTCCATAG | GAAGGGTCTCACTCGCTCTG |
| TSC2 | ENST00000219476 | 20 | chr16:2062847_2062989 | TGTGTTACTTGGCAGGCACTC | GAGCCAACTCACTCATCCCTG |
| TSC2 | ENST00000219476 | 21 | chr16:2064198_2064395 | CTAAGCCTCGCTGCTGTTCTC | GCGAGAGACCCAGGTTCC |
| TSC2 | ENST00000219476 | 22 | chr16:2065797_2065898 | CGTGGCCTTCTCTCTCTG | TGATGAACCACATGGCTATGAC |
| TSC2 | ENST00000219476 | 23 | chr16:2066066_2066176 | CACCTGCCTGTCACTCTGC | AGCAGTATGCCAGTGTGTTCG |
| TSC2 | ENST00000219476 | 24 | chr16:2066469_2066591 | CTAGCCTGCAGCCTTGTCCC | ACAGGACCCATTTCCACTCAC |
| TSC2 | ENST00000219476 | 25 | chr16:2067596_2067732 | GATCTCTCCATTCCTGACCCTG | AGACGATGAGGTCATGCAAGC |
| TSC2 | ENST00000219476 | 26 | chr16:2068030_2069202 | AGCTTTGGCCCTTCTGTGATAG | AGAAGACAGGGAGGCGTGAAAC |
| TSC2 | ENST00000219476 | 27 | chr16:2069274_2069434 | CTGGACATGATGGCTCGATAC | CACGCACAGGGTGGACTTAG |
| TSC2 | ENST00000219476 | 28 | chr16:2069555_2069675 | AGGTGACTGACCTTCCTTTC | CCTTCCTGAACACTGGGACC |
| TSC2 | ENST00000219476 | 29 | chr16:2070163_2070383 | GGGAGCATTCAGCTTGAGG | AAATATCCCAAGAGGGCCAAG |

FROM FIG. 11E

| Gene | Transcript | # | Coordinates | Seq1 | Seq2 |
|---|---|---|---|---|---|
| TSC2 | ENST00000219476 | 30 | chr16:2071593_2071804 | GAGAACAATGGTGCTGAGGC | TGAGGATTGTGGGACGGAG |
| TSC2 | ENST00000219476 | 31 | chr16:2072434_2072510 | CAAGCCAAAGAGACATTCTGCAC | AGCTTGTAGCTAGCACTGGGC |
| TSC2 | ENST00000219476 | 32 | chr16:2073693_2073822 | CAGGAGAAGGCTGGTTCTCG | AAGTTCAGAGCCAGTTCCCAG |
| TSC2 | ENST00000219476 | 33 | chr16:2074226_2074641 | GTTGATGCCTGGCAGTTTCTC | CCTGCGGATGGAGGACAGATAG |
| TSC2 | ENST00000219476 | 33 | chr16:2074642_2074721 | GAACACGAAACTGCACAGGG | CGAGGTTACACCATCTCCGAC |
| TSC2 | ENST00000219476 | 34 | chr16:2074949_2075032 | GCTCTGTGTTCCTCCCTGTG | TCAAAGGACTGTGACTGTGGC |
| TSC2 | ENST00000219476 | 35 | chr16:2075228_2075328 | GCTAACCTGTCACTCGCACC | CTGGCCTAAGCTCCCTGTG |
| TSC2 | ENST00000219476 | 36 | chr16:2076191_2076385 | TGGAATGGATGGTCTTGTCTG | GGTAGCAGGACTGGATGGG |
| TSC2 | ENST00000219476 | 37 | chr16:2076730_2076877 | CTCAGGTTCCGAGCCTAACAG | AGGAGGACCTGCCACCAAC |
| TSC2 | ENST00000219476 | 38 | chr16:2077861_2077947 | CTGTCCCACCAGCTCACG | GGTGTCTAGAGTGCAACCAG |
| TSC2 | ENST00000219476 | 39 | chr16:2078046_2078145 | CTGGACTACGAGTGCAACCTG | GGTTGAGCGGCTATGATG |
| TSC2 | ENST00000219476 | 40 | chr16:2078225_2078331 | AGATCGTGTCTGACCGCAAC | CAGTAAGTCTGGGAGGCGTG |
| TSC2 | ENST00000219476 | 41 | chr16:2078444_2078616 | CCTCTATGTCTGTGCACTGGG | AGCGGGTAGGGAATATGGG |

COORDINATES REFER TO HUMAN REFERENCE GENOME RELEASE hg18 (NCBI 36.1, MARCH 2006).
†M13 DENOTES THE UNIVERSAL SEQUENCING PRIMER 5'-GTAAAACGACGGCCAGT-3'.

FIG. 11F

GENES FREQUENTLY ALTERED IN PANCREATIC NEUROENDOCRINE TUMORS

This invention was made with funds from the United States government. The United States government retains rights in the invention according to the terms of grant nos. CA 57345, CA 62924, and CA 121113 from the National Institutes of Health.

TECHNICAL FIELD OF THE INVENTION

This invention is related to the area of identifying, treating, and predicting outcome for pancreatic tumors. In particular, it relates to pancreatic neuroendocrine tumors.

BACKGROUND OF THE INVENTION

Pancreatic Neuroendocrine Tumors (PanNETs) are the second most common malignancy of the pancreas. The ten-year survival rate is only 40% (1-3). They are usually sporadic, but they can arise in multiple endocrine neoplasia type 1 and more rarely in other syndromes, including von Hippel-Lindau (VHL) syndrome and tuberous sclerosis (4). "Functional" PanNETs secrete hormones that cause systemic effects, while "Nonfunctional" PanNETs do not and therefore cannot always be readily distinguished from other neoplasms of the pancreas. Non-functional PanNETs grow silently and patients may present with either an asymptomatic abdominal mass or symptoms of abdominal pain secondary to compression by a large tumor. Surgical resection is the treatment of choice, but many patients present with unresectable tumors or extensive metastatic disease, and medical therapies are relatively ineffective.

There is currently insufficient information about this tumor to either predict prognosis of patients diagnosed with PanNETs or to develop companion diagnostics and personalized treatments to improve disease management. Biallelic inactivation of the MEN1 gene, usually by a mutation in one allele coupled with loss of the remaining wild-type allele, occurs in 25-30% of PanNETs (5, 6). Chromosomal gains and losses, and expression analyses, have identified candidate loci for genes involved in the development of PanNETs, but these have not been substantiated by genetic or functional analyses (7-9).

There is a continuing need in the art to identify appropriate therapies and to predict outcome of patients with pancreatic tumors.

SUMMARY OF THE INVENTION

According to one aspect of the invention a method is provided for determining an appropriate therapy for an individual with a pancreatic neuroendocrine tumor. Tumor tissue or tumor cells or nucleic acid shed from the tumor are tested for a mutation in a gene selected from the group consisting of Rheb, AMPK, mTOR (FRAP1), TSC1, TSC2, IRS1, PI3KCA, AKT, PTEN, ERK1/2, p38MAPK, MK2, LKB1, GSK3β, RPS6KB1 (S6K1), and 4E-BP1. Identification of the presence of the mutation is a factor considered for treating the individual with an mTOR inhibitor.

Another aspect of the invention is a method for predicting outcome for a patient with a pancreatic neuroendocrine tumor. The pancreatic neuroendocrine tumor, or cells or nucleic acids shed from the tumor, are tested for the presence of an inactivating mutation in MEN1, DAXX, or ATRX. A mutation in at least one of these genes is a positive prognostic indicator.

An additional aspect of the invention is an isolated nucleic acid which comprises at least 20 nucleotides of a gene selected from MEN1, DAXX, ATRX, PTEN, TSC2, PIK3CA, and TP53. The nucleic acid comprises a mutation shown in Table 1.

Yet another aspect of the invention is a method of identifying a pancreatic neuroendocrine tumor. The pancreatic neuroendocrine tumor, or cells or nucleic acids shed from the tumor, is tested for any of the mutations shown in Table S2 or Table 1. Identification of any one of the mutations may be used to identify the tumor. Such markers can be used as a personal marker of the tumor, for example, for monitoring disease.

Yet another aspect of the invention is a method for distinguishing between a pancreatic neuroendocrine and a pancreatic ductal adenocarcinoma. The pancreatic neuroendocrine tumor, or cells or nucleic acids shed from the tumor, are tested for one or more mutations in one or more characteristic genes of each of a first group of genes and a second group of genes. The first group consists of MEN1, DAXX, and ATRX, and the second group consists of KRAS, CDKN2A, TGFBR1, SMAD3, and SMAD4. A mutation in the first group indicates a pancreatic neuroendocrine tumor. A mutation in the second group indicates a pancreatic ductal adenocarcinoma. Mutations can be detected using nucleic acid based or protein based assays.

These and other embodiments which will be apparent to those of skill in the art upon reading the specification provide the art with diagnostic and prognostic tools for better care of pancreatic tumor patients.

BRIEF DESCRIPTION OF THE DRAWINGS

FIGS. 1A-1B provide examples of traces showing mutations in DNA isolated from cancer cells (bottom panels of each), but not from normal cells of the same patient (top panels of each). FIG. 1C: Immunohistochemical staining with antibodies against DAXX shows lack of nuclear staining in cancer cells with the indicated mutation. Staining in the non-neoplastic cells (stroma) served as an internal control. FIG. 1D: Similar staining of another tumor with an antibody against ATRX protein. In both FIGS. 1C and 1D, although shown in black and white, nuclei that do not react with antibodies were blue because of the counterstain, while those that do react were brown.

(FIG. 2A) Patients with a DAXX or ATRX gene mutation vs. patients in whom both genes were wild-type (WT) (Hazard Ratio 0.22, 95% CI 0.06 to 0.84, p=0.03). (FIG. 2B) Patients with mutations in MEN1 as well as either DAXX or ATRX vs. those in which all three genes were WT (Hazard Ratio 0.07, 95% CI 0.008 to 0.51, p=0.01).

FIGS. 3A-3C. (Table (1)) show mutations in MEN1, DAXX, ATRX, PTEN, TSC2, PIK3CA, and TP53 in human pancreatic neuroendocrine tumors.

FIGS. 4A-4C. (Table (S1)) show a summary of sequence analysis of PanNETs

FIGS. 5A-5H. (Table (S2)) show mutations identified in the discovery set

FIG. 6. Table (S3) showing a comparison of commonly mutated genes in Pan NETs and PDAC.

FIG. 7. Table (S4) showing a comparison of somatic point mutations spectra in PanNETs and PaCa.

FIG. 8. Table (S5) showing immunohistochemistry (IHC) of ATRX and DAXX.

FIG. 9. Table (S6) showing patient characteristics.

FIG. 10. Table (S7) showing survival estimates.

Figure 11C:
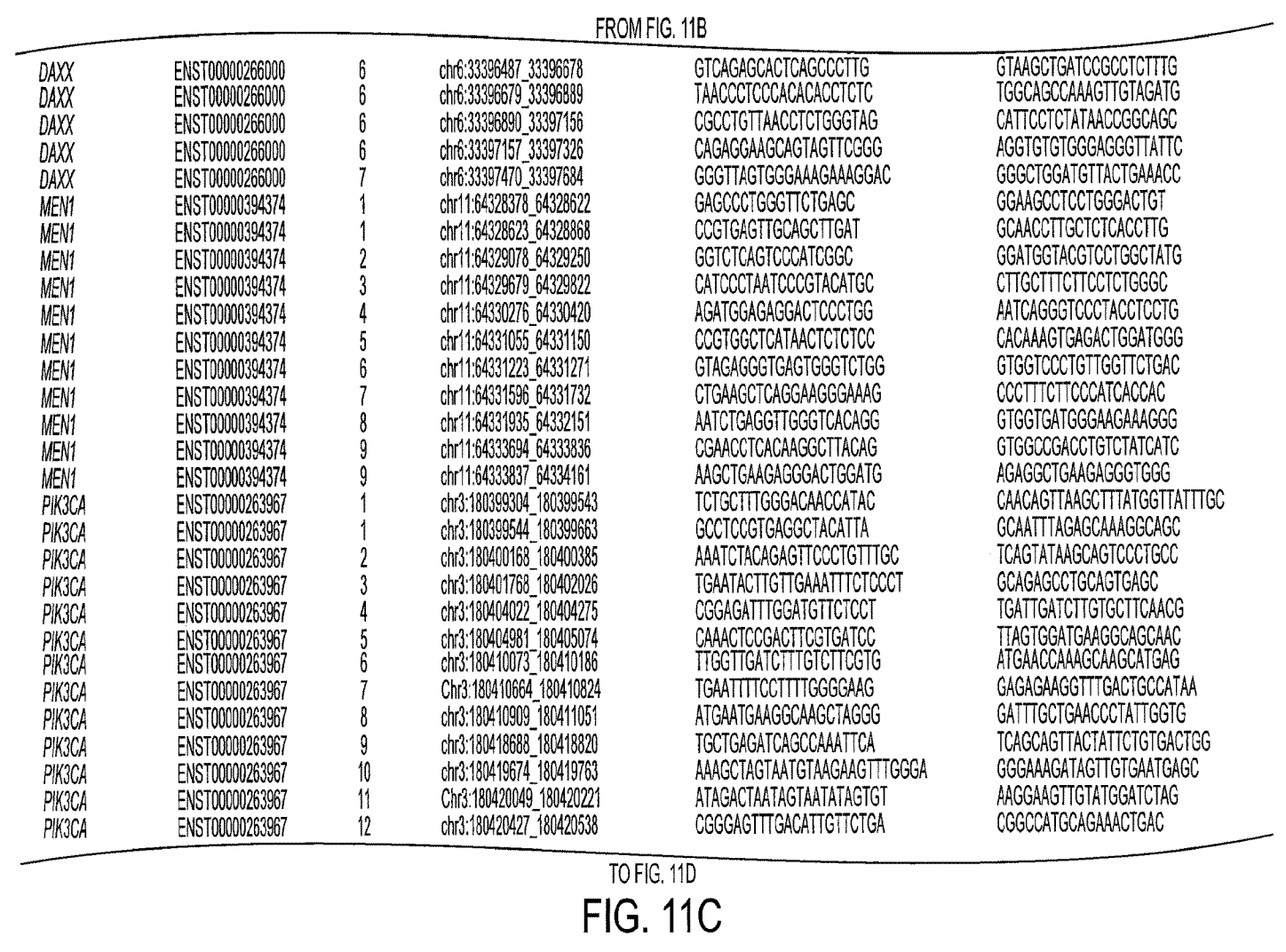

FIGS. 11A-11F. (Table (S8)) show primers used for PCR amplification and sequencing (SEQ ID NO: 1-291, in the order presented).

DETAILED DESCRIPTION OF THE INVENTION

Figures 1A, 1B, 1C, 1D:
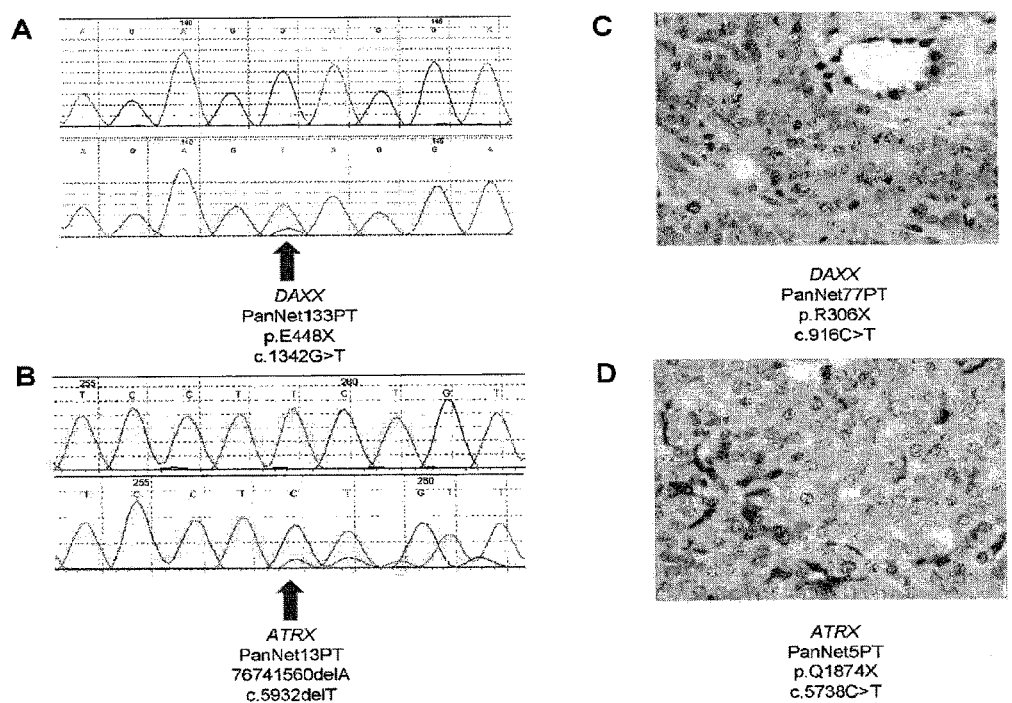
FIG. 1A-1D.

The inventors have used whole exome sequencing of pancreatic neuroendocrine tumors to identify tumor suppressor genes and to illuminate the genetic differences between the two major cancers of the pancreas. The mutations may be used to aid prognosis and provide a way to prioritize patients for therapy with mTOR inhibitors.

Samples from patients can be tested to determine an appropriate therapy, to predict outcome or course of disease, and to identify a pancreatic tumor or tumor type. Suitable samples for genetic testing include tumor cells, tumor tissues, biopsy samples, circulating tumor cells, circulating plasma DNA from cancer cells, archived samples, nucleic acids shed into a body fluid, such as gastroduodenal fluid or lymph. Collection and preparation of such samples for genetic testing is known in the art and any such techniques may be used.

Mutations can be identified in any available genetic material, including, for example, genomic DNA, cDNA, and RNA. Techniques for testing for mutations are legion and any such techniques may be used. Mutations can be identified by sequencing, by hybridization to probes, by amplification using specific primers, by primer extension, by ligation assay, etc. Combinations of such techniques can be used as well. Any technique can be selected and applied using the ordinary skill level in the art. Identified mutation can be used as a personal marker of the tumor, for example, for monitoring disease. Other uses are discussed below.

Mutations in the mTOR signaling pathway occur in pancreatic neuroendocrine tumors. The mutations may be in an gene of the pathway, including but not limited to Rheb, AMPK, mTOR (FRAP1), TSC1, TSC2, IRS1, PI3KCA, AKT, PTEN, ERK1/2, p38MAPK, MK2, LKB1, GSK3β, RPS6KB1 (S6K1), and 4E-BP1. Identification of mutations in this pathway can be used to identify patients that are likely to benefit most from use of mTOR inhibitors such as evorolimus, rapamycin, deforolimus, and temsirolimus.

Mutations in other genes, particularly MEN1, DAXX, and ATRX, have been found to be positive prognostic indicators. These appear to be tumor suppressor genes because of their mutational spectra. They also appear to be strong prognostic indicators of longer survival, either alone or in combination.

Nucleic acids can be used as probes or primers for mutations identified. Typically these probes or primers are oligonucleotides of at least 18, 20, 25, or 30 bases in length. Typically they are less than 100, 50, or 40 bases in length. If they contain one of the mutated bases they can be used as specific primers or probes for the mutation. Specific mutations are identified in Table 1. The oligonucleotides can optionally be labeled with a detectable moiety, such as a radioactive or fluorescent moiety. Alternatively, primers can be used which do not contain a mutation but may bracket a mutation, so that an amplicon is formed that contains the mutation. Adjacent primers to a mutation may also be used in assays employing a single base extension reaction. Amplicons may be of any size, but typically will be less than 500 base pairs, less than 250 bp, or less than 100 bp. Typically an amplicon will be greater than 35 bp, greater than 50 bp, or greater than 75 bp. Identification of any of the specific mutations listed in FIG. 3 or 4 (Tables 1 or S1) can be used to identify a pancreatic neuroendocrine tumor. The nucleic acid probes or primers may be used to identify them or other methods such as sequencing may be used.

Interestingly, different mutation spectra have been found for pancreatic neuroendocrine tumors and pancreatic ductal adenocarcinomas. Mutations in certain genes are highly characteristic of each type of pancreatic cancer. In the case of pancreatic neuroendocrine tumors, mutations in MEN1, DAXX, and ATRX occur frequently, but almost never in pancreatic ductal adenocarcinomas. Conversely, mutations in KRAS, CDKN2A, TGFBR1, SMAD3, and SMAD4 occur frequently in pancreatic ductal adenocarcinomas, but almost never in pancreatic neuroendocrine tumors. MTOR mutations occur much more frequently, but not exclusively, in pancreatic neuroendocrine tumors than in pancreatic ductal adenocarcinomas. Mutations in TP53 occur far more frequently, but not exclusively, in pancreatic ductal adenocarcinomas than in pancreatic neuroendocrine tumors. Thus these distinct mutation patterns can be used to distinguish these two tumors of the pancreas. These mutation patterns can be determined using nucleic acid based tests, using protein and/or antibody based tests, or using a combination of such tests. For example, immunohistochemical assays can be used to detect inactivating mutations in MEN1, DAXX, and ATRX. Absence of labeling indicates an inactivating mutation.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1—Sample Selection, Preparation, and Decoding

To gain insights into the genetic basis of this tumor type, we determined the exomic sequence of ~18,000 protein-coding genes in a Discovery set of ten well-characterized sporadic PanNETs. A clinically homogeneous set of tumors of high neoplastic cellularity is essential for the successful identification of genes and pathways involved in any tumor type. Thus, we excluded small cell and large neuroendocrine carcinomas and studied only samples that were not part of a familial syndrome. We macrodisected them to achieve a neoplastic cellularity of >80%. DNA from the enriched neoplastic samples and from matched non-neoplastic tissue from ten patients was used to prepare fragment libraries suitable for massively parallel sequencing. The coding sequences were enriched by capture with the SureSelect Enrichment System and sequenced using an Illumina GAIIx platform (10). The average coverage of each base in the targeted regions was 101-fold and 94.8 of the bases were represented by at least 10 reads (table S1).

Example 2—Mutation Analysis in Discovery Set

We identified 157 somatic mutations in 158 genes among the ten tumors used in the Discovery set. The mutations per tumor ranged from 8 to 23, with a mean of 16 (table S2). There were some obvious differences between the genetic landscapes of PanNETs and those of pancreatic ductal adenocarcinomas (PDAC, ref. 11). First, there were 60% fewer genes mutated per tumor in PanNETs than in PDACs. Second, the genes most commonly affected by mutation in PDACs (KRAS, TGF-β pathway, CDKN2A, TP53) were rarely altered in PanNETs and vice versa (table S3). Third, the spectrum of mutations in PDAC and PanNET were different, with C to T transitions more common in PDACs than in PanNETs, and C to G transversions more common in PanNETs than in PDACs (table S4). This suggests that PanNETs are exposed to different environmental carcinogens or that they harbor different repair pathways than PDACs.

Example 3—Mutation Analysis in Validation Set

Four genes were mutated in at least two tumors in the Discovery set: MEN1 in five, DAXX in three, PTEN in two, and TSC2 in two. Somatic mutations in each of these genes were confirmed by Sanger sequencing. The sequences of these genes were then determined by Sanger sequencing in a Validation set consisting of 58 additional PanNETs and their corresponding normal tissues (FIG. 1a,b). Although ATRX was mutated in only one sample in the Discovery set, it was included in the list of genes for further evaluation in the Validation set because its product forms a heterodimer with DAXX and therefore is part of the same pathway. Similarly, PIK3CA was included because it is considered to be part of the mTOR pathway that includes PTEN and TSC2 (12-14), in total, somatic mutations in MEN1, DAXX, ATRX, PTEN, TSC2, and PIK3CA were identified in 44.1%, 25%, 17.6%, 7.3%, 8.8%, and 1.4% PanNETs, respectively (Table 1).

Example 4—MEN1 Mutations

Of the 30 mutations in MEN1, 25 were inactivating mutations (18 insertions or deletions (indels), 5 nonsense and 2 splice-site mutations), while five were missense. At least 11 were homozygous; in the others, the presence of "contaminating" DNA from normal cells made it difficult to reliably distinguish heterozygous from homozygous changes. MEN1 encodes menin which is a nuclear protein that acts as a scaffold to regulate gene transcription by coordinating chromatin remodeling. It is an essential component of the MLL SET1-like histone methyltransferase (HMT) complex (15-19).

Example 5—DAXX and ATRX Mutations

DAXX was mutated in 17 and ATRX in 12 different PanNETs out of the 68 tested; thus, 42.6% of PanNETs had mutations in this pathway. There were 11 insertions or deletions (indels) and 4 nonsense mutations in DAXX, and six indels and 3 nonsense mutations in ATRX. The three ATRX missense mutations were within the conserved helicase domain and the DAXX missense mutations were non-conserved changes. Five DAXX and four ATRX mutations were homozygous, indicating loss of the other allele. The high ratio of inactivating to missense mutations in both genes unequivocally establishes them as PanNET tumor suppressor genes.

Loss of immunolabeling for DAXX and ATRX correlated with mutation of the respective gene (FIG. 1c, d and table S5). From these data, we assume that both copies of DAXX are generally inactivated, one by mutation and the other either by loss of the non-mutated allele or by epigenetic silencing. We also assume that both copies of ATRX are inactivated, one by mutation and the other by chromosome X inactivation. Recently, it has been shown that DAXX is an H3.3-specific histone chaperone (20). ATRX codes for a protein that at the amino-terminus has an ADD (ATRX-DNMTT3-DNMT3L) domain and a carboxy-terminal helicase domain. Almost all missense disease-causing mutations are within these two domains (21). DAXX and ATRX interact and both are required for H3.3 incorporation at the telomeres and ATRX is also required for suppression of telomeric repeat-containing RNA expression (22-24). ATRX was recently Shown to target CpG islands and G-rich tandem repeats (25), which exist close to telomeric regions.

Example 6—PTEN, TSC2, PIK3CA Mutations and Therapeutic Selection

We identified five PTEN mutations, two indels and three missense; six TSC2 mutations, one indel, one nonsense and three missense; and one PIK3CA missense mutation. Previously published expression analyses have suggested that the PIK3CA/AKT/mTOR axis is altered in most PanNETs (26). Our data suggest that, at least at the genetic level, only a subset of PanNETs have alterations of this pathway. This finding may have direct clinical application through prioritization of patients for therapy with mTOR pathway inhibitors. Everolimus (Afinitor, RAD-001, 40-O-(hydroxyethyl)-rapamycin) has been shown to increase progression-free survival in a subset of PanNET patients with advanced disease (27). If the mutational status of genes coding for proteins in the mTOR pathway predicts clinical response to mTOR inhibitors, it should be possible to select patients who would benefit most from an mTOR inhibitor through analysis of these genes in patients' tumors (29, 30).

Example 7—Prognosis

Figures 2A, 2B:
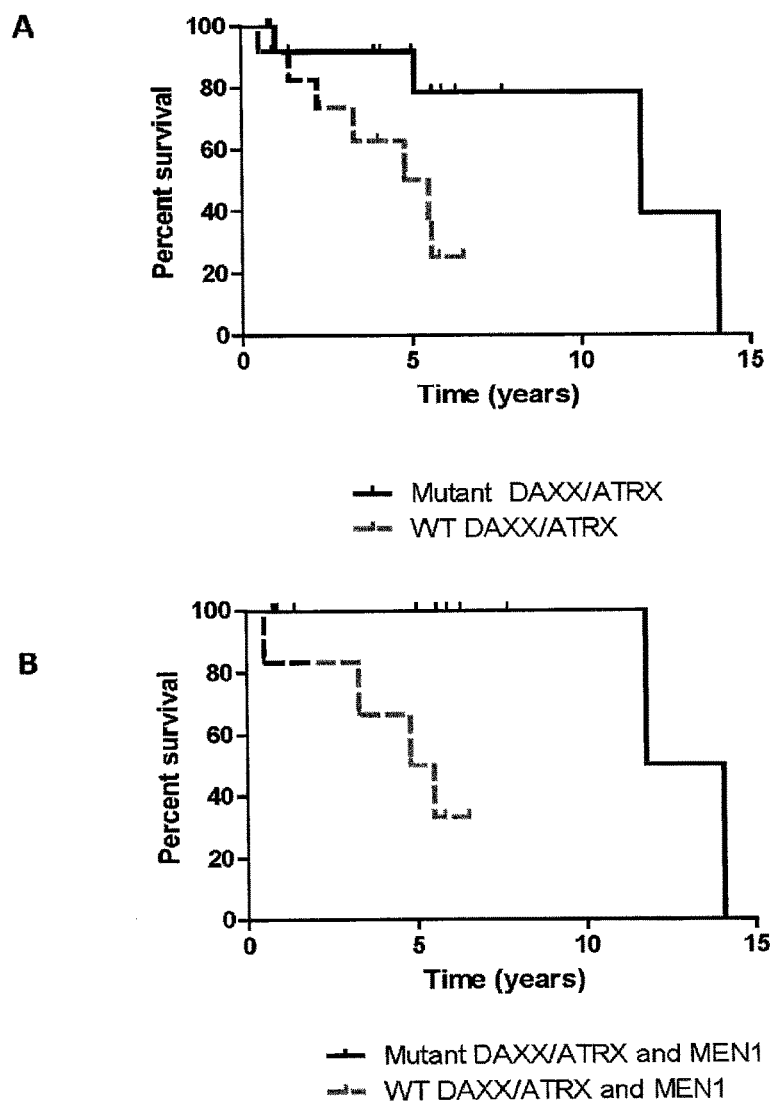
FIG. 2A-2B: Kaplan-Meier plots of overall survival in patients with metastatic PanNETs.

All 68 tumors evaluated in this study were from patients undergoing aggressive intervention (table S6) and included patients undergoing curative resection as well as those with metastatic disease. Interestingly, mutations in MEN1, DAXX/ATRX or the combination of both MEN1 and DAXX/ATRX showed prolonged survival relative to those patients without these mutations (FIG. 2A and table S7). This was particularly evident in patients with metastatic disease and with mutations in both MEN1 and DAXX/ATRX: 100% of patients with these mutations survived at least ten years while over 60% of the patients without these mutations died within five years of diagnosis (FIG. 2B). One possible explanation for the difference in survival is that mutations in MEN1 and DAXX/ATRX identify a biologically specific subgroup of PanNETs.

Example 8—Materials and Methods

Preparation of Illumina Genomic DNA Libraries

Fresh-frozen surgically resected tumor and normal tissues were obtained from patients under an Institutional Review Board protocol. Genomic DNA libraries were prepared following Illumina's (Illumina, San Diego, Calif.) suggested protocol with the following modifications. (1) 3 micrograms (µg) of genomic DNA from tumor or normal cells in 100 microliters (µl) of TE was fragmented in a Covaris sonicator (Covaris, Woburn, Mass.) to a size of 100-500 bp. To remove fragments shorter than 150 bp, DNA was mixed with 25 µl of 5× Phusion HF buffer, 416 µl of ddH2O, and 84 µl of NT binding buffer and loaded into NucleoSpin column (cat#636972, Clontech, Mountain View, Calif.). The column was centrifuged at 14000 g in a desktop centrifuge for 1 min, washed once with 600 µl of wash buffer (NT3 from Clontech), and centrifuged again for 2 min to dry completely.

DNA was eluted in 45 µl of elution buffer included in the kit. (2) Purified, fragmented DNA was mixed with 40 µl of H2O, 10 µl of End Repair Reaction Buffer, 5 µl of End Repair Enzyme Mix (cat# E6050, NEB, Ipswich, Mass.). The 100 µl end-repair mixture was incubated at 20° C. for 30 min, purified by a PCR purification kit (Cat #28104, Qiagen) and eluted with 42 µl of elution buffer (EB). (3) To A-tail, all 42 µl of end-repaired DNA was mixed with 5 µl of 10× dA Tailing Reaction Buffer and 3 µl of Klenow (exo-)(cat# E6053, NEB, Ipswich, Mass.). The 50 µl mixture was incubated at 37° C. for 30 min before DNA was purified with a MinElute PCR purification kit (Cat #28004, Qiagen). Purified DNA was elated with 25 µl of 70° C. EB. (4) For adaptor ligation, 25 µl of A-tailed DNA was mixed with 10 µl of PE-adaptor (Illumina), 10 µl of 5× Ligation buffer and 5 µl of Quick T4 DNA ligase (cat# E6056, NEB, Ipswich, Mass.). The ligation mixture was incubated at 20° C. for 15 min. (5) To purify adaptor-ligated DNA, 50 µl of ligation mixture from step (4) was mixed with 200 µl of NT buffer and cleaned up by NucleoSpin column. DNA was eluted in 50 µl elution buffer. (6) To obtain an amplified library, ten PCRs of 50 µl each were set up, each including 29 µl of H2O, 10 µl of 5× Phusion HF buffer, 1 µl of a dNTP mix containing 10 mM of each dNTP, 2.5 µl of DMSO, 1 µl of Illumina PE primer #1, 1 µl of Illumina PE primer #2, 0.5 µl of Hotstart Phusion polymerase, and 5 µl of the DNA from step (5). The PCR program used was: 98° C. 2 minute; 6 cycles of 98° C. for 15 seconds, 65° C. for 30 seconds, 72° C. for 30 seconds; and 72° C. for 5 min. To purify the PCR product, 500 µl. PCR mixture (from the ten PCR reactions) was mixed with 1000 µl NT buffer from a NucleoSpin Extract II kit and purified as described in step (1). Library DNA was eluted with 70° C. elution buffer and the DNA concentration was estimated by absorption at 260 nm.

Exome and Targeted Subgenomic DNA Capture

Human exome capture was performed following a protocol from Agilent's SureSelect Paired-End Version 2.0 Human Exome kit (Agilent, Santa Clara, Calif.) with the following modifications, (1) A hybridization mixture was prepared containing 25 µl of SureSelect Hyb #1, 1 µl of SureSelect Hyb #2, 10 µl of SureSelect Hyb #3, and 13 µl of SureSelect Hyb #4. (2) 3.4 µl (0.5 µg) of the PE-library DNA described above, 2.5 µl of SureSelect Block #1, 2.5 µl of SureSelect Block #2 and 0.6 µl of Block #3; was loaded into one well in a 384-well Diamond PCR plate (cat# AB-1111, Thermo-Scientific, Lafayette, Colo.), sealed with microAmp clear adhesive film (cat#4306311; ABI, Carlsbad, Calif.) and placed in GeneAmp PCR system 9700 thermocycler (Life Sciences Inc., Carlsbad Calif.) for 5 minutes at 95° C. then held at 65° C. (with the heated lid on). (3) 25-30 µl of hybridization buffer from step (1) was heated for at least 5 minutes at 65° C. in another sealed plate with heated lid on. (4) 5 µl of SureSelect Oligo Capture Library, 1 µl of nuclease-free water, and 1 µl of diluted RNase Block (prepared by diluting RNase Block 1:1 with nuclease-free water) were mixed and heated at 65° C. for 2 minutes in another sealed 384-well plate. (5) While keeping all reactions at 65° C., 13 µl of Hybridization Buffer from Step (3) was added to the 7 µl of the SureSelect Capture Library Mix from Step (4) and then the entire contents (9 µl) of the library from Step (2). The mixture was slowly pipetted up and down 8 to 10 times. (6) The 384-well plate was sealed tightly and the hybridization mixture was incubated for 24 hours at 65° C. with a heated lid.

After hybridization, five steps were performed to recover and amplify captured DNA library: (1) Magnetic beads for recovering captured DNA: 50 µl of Dynal MyOne Streptavidin C1 magnetic beads (Cat #650.02, Invitrogen Dynal, AS Oslo, Norway) was placed in a 1.5 ml microfuge tube and vigorously resuspended on a vortex mixer. Beads were washed three times by adding 200 µl of SureSelect Binding buffer, mixed on a vortex for five seconds, then removing and discarding supernatant after placing the tubes in a Dynal magnetic separator. After the third wash, beads were resuspended in 200 µl of SureSelect Binding buffer. (2) To bind captured DNA, the entire hybridization mixture described above (29 µl) was transferred directly from the thermocycler to the bead solution and mixed gently; the hybridization mix/bead solution was incubated an Eppendorf thermomixer at 850 rpm for 30 minutes at room temperature. (3) To wash the beads, the supernatant was removed from beads after applying a Dynal magnetic separator and the beads was resuspended in 500 µl SureSelect Wash Buffer #1 by mixing on vortex mixer for 5 seconds and incubated for 15 minutes at room temperature. Wash Buffer#1 was then removed from beads after magnetic separation. The beads were further washed three times, each with 500 µl pre-warmed SureSelect Wash Buffer #2 after incubation at 65° C. for 10 minutes. After the final wash, SureSelect Wash Buffer #2 was completely removed. (4) To elute captured DNA, the beads were suspended in 50 µl SureSelect Elution Buffer, vortex-mixed and incubated for 10 minutes at room temperature. The supernatant was removed after magnetic separation, collected in a new 1.5 ml microcentrifuge tube, and mixed with 50 µl of SureSelect Neutralization Buffer. DNA was purified with a Qiagen MinElute column and eluted in 17 µl of 70° C. EB to obtain 15 µl of captured DNA library. (5) The captured DNA library was amplified in the following way: 15 PCR reactions each containing 9.5 µl of H2O, 3 µl of 5× Phusion HF buffer, 0.3 µl of 10 mM dNTP, 0.75 µl of DMSO, 0.15 µl of Illumina PE primer #1, 0.15 µl of Illumina PE primer #2, 0.15 µl of Hotstart Phusion polymerase, and 1 µl of captured exome library were set up. The PCR program used was: 98° C. for 30 seconds; 14 cycles of 98° C. for 10 seconds, 65° C. for 30 seconds, 72° C. for 30 seconds; and 72° C. for 5 min. To purify PCR products, 225 µl PCR mixture (from 15 PCR reactions) was mixed with 450 µl NT buffer from NucleoSpin Extract II kit and purified as described above. The final library DNA was eluted with 30 µl of 70° C. elution buffer and DNA concentration was estimated by OD260 measurement.

Somatic Mutation Identification by Massively Parallel Sequencing

Captured DNA libraries were sequenced with the lumina GAIIx Genome Analyzer, yielding 150 (2×75) base pairs from the final library fragments. Sequencing reads were analyzed and aligned to human genome hg 18 with the Eland algorithm in CASAVA 1.6 software (Illumina) A mismatched base was identified as a mutation only when (i) it was identified by more than three distinct tags; (ii) the number of distinct tags containing a particular mismatched base was at least 16% of the total distinct tags; and (iii) it was not present in >0.5% of the tags in the matched normal sample. SNP search databases included http://www.ncbi.nlm.nih.gov/projects/SNP/ and http://browser.1000genomes.org/index.html.

Evaluation of Genes in Additional Tumors and Matched Normal Controls

For the ATRX, DAXX, MEN1, PIK3CA, PTEN, TP53 and TSC2 genes, the coding region was sequenced in a validation Set, comprising a series of additional pancreatic neuroendocrine tumors and matched controls. PCR amplification and Sanger sequencing were performed following protocols described previously (1) using the primers listed in table S8.

Immunohistochemistry

Immunohistochemical labeling for ATRX and DAXX proteins was performed on formalin-fixed, paraffin-embedded sections of PanNETs. Heat-induced antigen retrieval was performed in a steamer using citrate buffer (pH 6.0) (Vector Laboratories) for 30 min followed by 10 min. of cooling. Endogenous peroxidase was blocked for 10 min with dual endogenous enzyme-blocking reagent (Dako). Serial sections were then incubated with primary antibody; anti-ATRX (1:400 dilution; catalog no. HPA001906. Sigma-Aldrich) and anti-DAXX (1:75 dilution; catalog no. HPA008736, Sigma-Aldrich) for 1 h at room temperature. The sections were then incubated for 30 min with secondary antibody (Leica Microsystems) followed by detection with 3,3'-Diaminobenzidine (Sigma-Adrich) for 8 min. Sections were washed with phosphate-buffered saline with 0.1% Tween-20. Finally, sections were counterstained with Harris hematoxylin, subsequently rehydrated and mounted. Only nuclear labeling of either protein was considered positive. At least 50% of the cells needed to have nuclear labeling for the marker to be considered positive. Internal controls included islets of Langerhans and endothelial cells (including within intra-tumoral vessels) which demonstrated strong nuclear labeling for both ATRX and DAXX.

Clinical Correlations

Clinical information on the patients evaluated in this study were obtained from the Johns Hopkins Hospital and the Memorial Sloan-Kettering Comprehensive Cancer Center in the context of approved IRB protocols. Clinical data were collected retrospectively and compared with mutational status. Overall survival was calculated from the time of diagnosis until death. Patients who were alive at the time of analysis were censored at the date of last observation. Survival curves were plotted by the Kaplan-Meier method and compared using the Mantel-Cox log-rank test (Prism, GraphPad Software, La Jolla, Calif.).

REFERENCES

The disclosure of each reference cited is expressly incorporated herein.

1. R. H. Wuhan, M. B. Pitman, D. S. Klimstra, *Tumors of the Pancreas. Atlas of Tumor Pathology* (American Registry of Pathology and Armed Forces Institute of Pathology, Washington, D.C., ed. Fourth Series, Fascicle 6, 2007).
2. M. Fredrich, A. Reisch, R. B. Illing, *Exp Brain Res* 195, 241 (2009).
3. S. Ekeblad, B. Skogseid, K. Dunder, K. Oberg, B. Eriksson, *Clin Cancer Res* 14, 7798 (2008).
4. P. Francalanci et al., *Am J Surg Pathol* 27, 1386 (2003).
5. V. Corbo et al., *Endocr Relat Cancer* 17, 771 (2010).
6. P. Capelli et al., Arch Pathol Lab Med 133, 350 (2009).
7. D. C. Chung et al., *Cancer Res* 58, 3706 (1998).
8. G. Floridia et al., *Cancer Genet. Cytogenet.* 156, 23 (2005).
9. W. Hu et al., *Genes Cancer* 1, 360 (2010).
10. See Example 8.
11. S. Jones et al., *Science* 321, 1801 (2008).
12. D. W. Parsons et al., *Nature* 436, 792 (2005).
13. D. A. Guertin, D. M. Sabatini, *Cancer Cell* 12, 9 (2007).
14. R. J. Shaw, L. C. Cantley, *Nature* 441, 424 (2006).
15. C. M. Hughes et al., *Mol Cell* 13, 587 (2004).
16. A. Yokoyama et al. *Mol Cell Biol* 24, 5639 (2004).
17. J. Grembecka, A. M. Belcher, T. Hartley, T. Cierpicki, *J Biol Chem.* October 20 epub ahead of print (2010).
18. H. Kim et al., *Cancer Res.* 63, 6135 (2003).
19. S. K. Agarwal et al., *Cell* 96, 143 (1999).
20. P, W. Lewis, S. J. Elsaesser, K. M. Noh, S. C. Stadler, C. D. Allis, *Proc Natl Acad Sci USA* 107, 14075 (2010).
21. R. J. Gibbons et al., *Human Mutation* 29, 796 (2008).
22. P. Drane, K. Ouararhni, A. Depaux, M. Shuaib, A. Hamiche, *Genes Dev* 24, 1253 (2010).
23. A. D. Goldberg et al., *Cell* 140, 678 (2010).
24. L. H. Wong et al., *Genome Res* 20, 351 (2010).
25. M. J. Law et al., *Cell* 143, 367 (2010).
26. E. Missiaglia et al., *J Clin Oncol* 28, 245 (2010).
27. C. W. Chiu, H. Nozawa, D. Hanahan, *J Clin Oncol* 28, 4425 (2010).
28. P. Liu, H. Cheng, T. M. Roberts, J. J. Zhao, *Nat Rev Drug Discov* 8, 627 (2009).
29. D. A. Krueger et al., *N Engl J Med* 363, 1801 (2010).
30. T. Sjoblom et al., *Science* 314, 268 (2006).

We claim:

1. A method, comprising:
   extracting nucleic acids from pancreatic neuroendocrine tumor of an individual;
   amplifying and sequencing exomic sequences of the extracted nucleic acids in genes TSC2, PIK3CA, IRS1, and PTEN;
   detecting a mutation in an exomic sequence of at least one of TSC2, PIK3CA, PTEN, or IRS1; and
   administering to the individual an mTOR inhibitor when the mutation is detected.

2. The method of claim 1, wherein the mTOR inhibitor is evorolimus.

3. The method of claim 1, wherein the mTOR inhibitor is rapamycin.

4. The method of claim 1, wherein the mTOR inhibitor is deforolimus.

5. The method of claim 1, wherein the mTOR inhibitor is temsirolimus.

6. The method of claim 1, additionally comprising amplifying and sequencing exomic sequences in genes TSC2, PIK3CA, IRS1, and PTEN from normal tissue of the individual.

7. The method of claim 1, wherein the amplifying or sequencing is performed using at least one primer selected from the group consisting of SEQ ID NOs: 63-83, 208-228, 84-92, 229-237, 104-145, and 249-290.

8. The method of claim 1, wherein the mutation comprises an indel, frameshift, or nonsense mutation.

9. The method of claim 1, wherein the mutation comprises a somatic mutation.

10. The method of claim 1, wherein the nucleic acids are extracted from resected tumor.

11. The method of claim 1, wherein the nucleic acids are extracted from a biopsy of the tumor.

12. The method of claim 1, further comprising the step of enriching the nucleic acids extracted from the tumor for exomic sequences.

13. The method of claim 7, wherein evorolimus is administered to the individual.

14. A method, comprising:
   extracting nucleic acids from a plasma sample of an individual with a pancreatic neuroendocrine tumor;
   amplifying and sequencing exomic sequences of the extracted nucleic acids in genes TSC2, PIK3CA, IRS1, and PTEN;
   detecting a mutation in an exomic sequence of at least one of TSC2, PIK3CA, PTEN, or IRS1, and
   administering to the individual an mTOR inhibitor when the mutation is detected.

15. The method of claim 14, wherein the amplifying or sequencing is performed using at least one primer selected from the group consisting of SEQ ID NOs: 63-83, 208-228, 84-92, 229-237, 104-145, and 249-290.

16. The method of claim 14, wherein the mutation comprises an indel, frameshift, or nonsense mutation.

17. The method of claim 14, wherein the mutation comprises a somatic mutation.

18. The method of claim 14, wherein the mTOR inhibitor is evorolimus.

19. The method of claim 14, wherein the mTOR inhibitor is rapamycin.

20. The method of claim 14, wherein the mTOR inhibitor is deforolimus.

21. The method of claim 14, wherein the mTOR inhibitor is temsirolimus.

22. The method of claim 14, further comprises the step of enriching the nucleic acids extracted from the plasma sample for exomic sequences.

* * * * *

SEQUENCE LISTING

```
<160> NUMBER OF SEQ ID NOS: 291

<210> SEQ ID NO 1
<211> LENGTH: 20
<212> TYPE: DNA
<213> ORGANISM: Homo sapiens

<400> SEQUENCE: 1
ggcatttaag gggaccaaac                                              20

<210> SEQ ID NO 2
<211> LENGTH: 21
<212> TYPE: DNA
<213> ORGANISM: Homo sapiens

<400> SEQUENCE: 2
caatgactat ccatccctcc a                                            21

<210> SEQ ID NO 3
<211> LENGTH: 20
```

```
<212> TYPE: DNA
<213> ORGANISM: Homo sapiens

<400> SEQUENCE: 3 agtaggggt ggagggtaca                                        20

<210> SEQ ID NO 4
<211> LENGTH: 20
<212> TYPE: DNA
<213> ORGANISM: Homo sapiens

<400> SEQUENCE: 4
gcatagggaa ccctcaacaa                                       20

<210> SEQ ID NO 5
<211> LENGTH: 21
<212> TYPE: DNA
<213> ORGANISM: Homo sapiens

<400> SEQUENCE: 5
ggggaatgtg ttcctaaaac c                                     21

<210> SEQ ID NO 6
<211> LENGTH: 27
<212> TYPE: DNA
<213> ORGANISM: Homo sapiens

<400> SEQUENCE: 6
cattttatta tccttgaaaa attctga                               27

<210> SEQ ID NO 7
<211> LENGTH: 21
<212> TYPE: DNA
<213> ORGANISM: Homo sapiens

<400> SEQUENCE: 7
ccaactttgt ttccctctct g                                     21

<210> SEQ ID NO 8
<211> LENGTH: 21
<212> TYPE: DNA
<213> ORGANISM: Homo sapiens

<400> SEQUENCE: 8
tgacactgtt ttgcaacctg a                                     21

<210> SEQ ID NO 9
<211> LENGTH: 24
<212> TYPE: DNA
<213> ORGANISM: Homo sapiens

<400> SEQUENCE: 9
gggtagtttt gtttcttttg ttgc                                  24

<210> SEQ ID NO 10
<211> LENGTH: 20
<212> TYPE: DNA
<213> ORGANISM: Homo sapiens

<400> SEQUENCE: 10
ttgcttgtat tggcctagca                                       20

<210> SEQ ID NO 11
```

-continued

```
<211> LENGTH: 22
<212> TYPE: DNA
<213> ORGANISM: Homo sapiens

<400> SEQUENCE: 11
tccatgataa aggcaacatt ca                                              22

<210> SEQ ID NO 12
<211> LENGTH: 22
<212> TYPE: DNA
<213> ORGANISM: Homo sapiens

<400> SEQUENCE: 12
ttctgcttcc aatagatgct tt                                              22

<210> SEQ ID NO 13
<211> LENGTH: 23
<212> TYPE: DNA
<213> ORGANISM: Homo sapiens

<400> SEQUENCE: 13
tgcaaaactg aaaagaaca aca                                              23

<210> SEQ ID NO 14
<211> LENGTH: 20
<212> TYPE: DNA
<213> ORGANISM: Homo sapiens

<400> SEQUENCE: 14
tgaaagagcg ggaaagaaaa                                                 20

<210> SEQ ID NO 15
<211> LENGTH: 24
<212> TYPE: DNA
<213> ORGANISM: Homo sapiens

<400> SEQUENCE: 15
tttcacagca gactaagatg aacc                                            24

<210> SEQ ID NO 16
<211> LENGTH: 20
<212> TYPE: DNA
<213> ORGANISM: Homo sapiens

<400> SEQUENCE: 16
tggcgacatt aagggtgatt                                                 20

<210> SEQ ID NO 17
<211> LENGTH: 22
<212> TYPE: DNA
<213> ORGANISM: Homo sapiens

<400> SEQUENCE: 17
ttcccactga aatatgcatc ac                                              22

<210> SEQ ID NO 18
<211> LENGTH: 20
<212> TYPE: DNA
<213> ORGANISM: Homo sapiens

<400> SEQUENCE: 18
gaaggaaagt ccccctgttc                                                 20
```

```
<210> SEQ ID NO 19
<211> LENGTH: 20
<212> TYPE: DNA
<213> ORGANISM: Homo sapiens

<400> SEQUENCE: 19
ccaccccact caccaattta                                              20

<210> SEQ ID NO 20
<211> LENGTH: 22
<212> TYPE: DNA
<213> ORGANISM: Homo sapiens

<400> SEQUENCE: 20
cattaataga aataaattaa gg                                           22

<210> SEQ ID NO 21
<211> LENGTH: 20
<212> TYPE: DNA
<213> ORGANISM: Homo sapiens

<400> SEQUENCE: 21
aacaaacctc ccctcaggat                                              20

<210> SEQ ID NO 22
<211> LENGTH: 20
<212> TYPE: DNA
<213> ORGANISM: Homo sapiens

<400> SEQUENCE: 22
tgaaggcatg gtcattcaga                                              20

<210> SEQ ID NO 23
<211> LENGTH: 20
<212> TYPE: DNA
<213> ORGANISM: Homo sapiens

<400> SEQUENCE: 23
cgaggcattt taaaggctga                                              20

<210> SEQ ID NO 24
<211> LENGTH: 24
<212> TYPE: DNA
<213> ORGANISM: Homo sapiens

<400> SEQUENCE: 24
ttggcctccc aaagtcctga gatt                                         24

<210> SEQ ID NO 25
<211> LENGTH: 24
<212> TYPE: DNA
<213> ORGANISM: Homo sapiens

<400> SEQUENCE: 25
aacttgcagg aagactgtga gcga                                         24

<210> SEQ ID NO 26
<211> LENGTH: 25
<212> TYPE: DNA
<213> ORGANISM: Homo sapiens

<400> SEQUENCE: 26
gagatccctg atactgaata ctagc                                        25
```

```
<210> SEQ ID NO 27
<211> LENGTH: 24
<212> TYPE: DNA
<213> ORGANISM: Homo sapiens

<400> SEQUENCE: 27
tttctgttca tcgctgcttc cctc                                          24

<210> SEQ ID NO 28
<211> LENGTH: 24
<212> TYPE: DNA
<213> ORGANISM: Homo sapiens

<400> SEQUENCE: 28
tcctttccct gttgacttct cagc                                          24

<210> SEQ ID NO 29
<211> LENGTH: 24
<212> TYPE: DNA
<213> ORGANISM: Homo sapiens

<400> SEQUENCE: 29
agcacttgct tgctgcttct tagg                                          24

<210> SEQ ID NO 30
<211> LENGTH: 24
<212> TYPE: DNA
<213> ORGANISM: Homo sapiens

<400> SEQUENCE: 30
aactgtgact catcctgctc acct                                          24

<210> SEQ ID NO 31
<211> LENGTH: 24
<212> TYPE: DNA
<213> ORGANISM: Homo sapiens

<400> SEQUENCE: 31
cctgttctgg ctctgtaacc tact                                          24

<210> SEQ ID NO 32
<211> LENGTH: 27
<212> TYPE: DNA
<213> ORGANISM: Homo sapiens

<400> SEQUENCE: 32
gagtaagcag atgacctaaa ttaccac                                       27

<210> SEQ ID NO 33
<211> LENGTH: 26
<212> TYPE: DNA
<213> ORGANISM: Homo sapiens

<400> SEQUENCE: 33
aggaaacact gaatgttagc tcatct                                        26

<210> SEQ ID NO 34
<211> LENGTH: 24
<212> TYPE: DNA
<213> ORGANISM: Homo sapiens

<400> SEQUENCE: 34
gaagtcttcc aagggcagat acca                                          24
```

```
<210> SEQ ID NO 35
<211> LENGTH: 20
<212> TYPE: DNA
<213> ORGANISM: Homo sapiens

<400> SEQUENCE: 35
aagcacatcc gattttccaa                                               20

<210> SEQ ID NO 36
<211> LENGTH: 26
<212> TYPE: DNA
<213> ORGANISM: Homo sapiens

<400> SEQUENCE: 36
gccatgtttg gtcgtttgta catagt                                        26

<210> SEQ ID NO 37
<211> LENGTH: 28
<212> TYPE: DNA
<213> ORGANISM: Homo sapiens

<400> SEQUENCE: 37
ctcagaatag tggttgacat gagttcag                                      28

<210> SEQ ID NO 38
<211> LENGTH: 24
<212> TYPE: DNA
<213> ORGANISM: Homo sapiens

<400> SEQUENCE: 38
tgggtatcag tagccttcga caca                                          24

<210> SEQ ID NO 39
<211> LENGTH: 24
<212> TYPE: DNA
<213> ORGANISM: Homo sapiens

<400> SEQUENCE: 39
acacccacaa ctgtaacatt tccc                                          24

<210> SEQ ID NO 40
<211> LENGTH: 24
<212> TYPE: DNA
<213> ORGANISM: Homo sapiens

<400> SEQUENCE: 40
taagcaacac acaggcctaa ccca                                          24

<210> SEQ ID NO 41
<211> LENGTH: 21
<212> TYPE: DNA
<213> ORGANISM: Homo sapiens

<400> SEQUENCE: 41
gggacagcta atgccaatct g                                             21

<210> SEQ ID NO 42
<211> LENGTH: 21
<212> TYPE: DNA
<213> ORGANISM: Homo sapiens

<400> SEQUENCE: 42
```

```
gtctgctggg agagactgga c                                              21

<210> SEQ ID NO 43
<211> LENGTH: 21
<212> TYPE: DNA
<213> ORGANISM: Homo sapiens

<400> SEQUENCE: 43
caaaggacgc atagtgtcac c                                              21

<210> SEQ ID NO 44
<211> LENGTH: 21
<212> TYPE: DNA
<213> ORGANISM: Homo sapiens

<400> SEQUENCE: 44
cgcctccatt gaaggaagta g                                              21

<210> SEQ ID NO 45
<211> LENGTH: 21
<212> TYPE: DNA
<213> ORGANISM: Homo sapiens

<400> SEQUENCE: 45
gaaaggtttc aaacaggtgg c                                              21

<210> SEQ ID NO 46
<211> LENGTH: 21
<212> TYPE: DNA
<213> ORGANISM: Homo sapiens

<400> SEQUENCE: 46
catcagtcaa cctggactcc c                                              21

<210> SEQ ID NO 47
<211> LENGTH: 21
<212> TYPE: DNA
<213> ORGANISM: Homo sapiens

<400> SEQUENCE: 47
gtaagctgat ccgcctcttt g                                              21

<210> SEQ ID NO 48
<211> LENGTH: 21
<212> TYPE: DNA
<213> ORGANISM: Homo sapiens

<400> SEQUENCE: 48
tggcagccaa agttgtagat g                                              21

<210> SEQ ID NO 49
<211> LENGTH: 21
<212> TYPE: DNA
<213> ORGANISM: Homo sapiens

<400> SEQUENCE: 49
cattcctcta taaccggcag c                                              21

<210> SEQ ID NO 50
<211> LENGTH: 21
<212> TYPE: DNA
<213> ORGANISM: Homo sapiens

<400> SEQUENCE: 50
```

```
aggtgtgtgg gagggttatt c                                        21

<210> SEQ ID NO 51
<211> LENGTH: 21
<212> TYPE: DNA
<213> ORGANISM: Homo sapiens

<400> SEQUENCE: 51
gggctggatg ttactgaaac c                                        21

<210> SEQ ID NO 52
<211> LENGTH: 19
<212> TYPE: DNA
<213> ORGANISM: Homo sapiens

<400> SEQUENCE: 52
ggaagcctcc tgggactgt                                           19

<210> SEQ ID NO 53
<211> LENGTH: 20
<212> TYPE: DNA
<213> ORGANISM: Homo sapiens

<400> SEQUENCE: 53
gcaaccttgc tctcaccttg                                          20

<210> SEQ ID NO 54
<211> LENGTH: 21
<212> TYPE: DNA
<213> ORGANISM: Homo sapiens

<400> SEQUENCE: 54
ggatggtacg tcctggctat g                                        21

<210> SEQ ID NO 55
<211> LENGTH: 20
<212> TYPE: DNA
<213> ORGANISM: Homo sapiens

<400> SEQUENCE: 55
cttgctttct tcctctgggc                                          20

<210> SEQ ID NO 56
<211> LENGTH: 21
<212> TYPE: DNA
<213> ORGANISM: Homo sapiens

<400> SEQUENCE: 56
aatcagggtc cctacctcct g                                        21

<210> SEQ ID NO 57
<211> LENGTH: 21
<212> TYPE: DNA
<213> ORGANISM: Homo sapiens

<400> SEQUENCE: 57
cacaaagtga gactggatgg g                                        21

<210> SEQ ID NO 58
<211> LENGTH: 21
<212> TYPE: DNA
<213> ORGANISM: Homo sapiens
```

```
<400> SEQUENCE: 58
gtggtccctg ttggttctga c                                              21

<210> SEQ ID NO 59
<211> LENGTH: 20
<212> TYPE: DNA
<213> ORGANISM: Homo sapiens

<400> SEQUENCE: 59
ccctttcttc ccatcaccac                                                20

<210> SEQ ID NO 60
<211> LENGTH: 20
<212> TYPE: DNA
<213> ORGANISM: Homo sapiens

<400> SEQUENCE: 60
gtggtgatgg gaagaaaggg                                                20

<210> SEQ ID NO 61
<211> LENGTH: 21
<212> TYPE: DNA
<213> ORGANISM: Homo sapiens

<400> SEQUENCE: 61
gtggccgacc tgtctatcat c                                              21

<210> SEQ ID NO 62
<211> LENGTH: 19
<212> TYPE: DNA
<213> ORGANISM: Homo sapiens

<400> SEQUENCE: 62
agaggctgaa gagggtggg                                                 19

<210> SEQ ID NO 63
<211> LENGTH: 27
<212> TYPE: DNA
<213> ORGANISM: Homo sapiens

<400> SEQUENCE: 63
caacagttaa gctttatggt tatttgc                                        27

<210> SEQ ID NO 64
<211> LENGTH: 21
<212> TYPE: DNA
<213> ORGANISM: Homo sapiens

<400> SEQUENCE: 64
gcaatttaga gcaaaggcag c                                              21

<210> SEQ ID NO 65
<211> LENGTH: 21
<212> TYPE: DNA
<213> ORGANISM: Homo sapiens

<400> SEQUENCE: 65
tcagtataag cagtccctgc c                                              21

<210> SEQ ID NO 66
<211> LENGTH: 18
<212> TYPE: DNA
<213> ORGANISM: Homo sapiens
```

```
<400> SEQUENCE: 66
gcagagcctg cagtgagc                                                    18

<210> SEQ ID NO 67
<211> LENGTH: 22
<212> TYPE: DNA
<213> ORGANISM: Homo sapiens

<400> SEQUENCE: 67
tgattgatct tgtgcttcaa cg                                               22

<210> SEQ ID NO 68
<211> LENGTH: 21
<212> TYPE: DNA
<213> ORGANISM: Homo sapiens

<400> SEQUENCE: 68
ttagtggatg aaggcagcaa c                                                21

<210> SEQ ID NO 69
<211> LENGTH: 21
<212> TYPE: DNA
<213> ORGANISM: Homo sapiens

<400> SEQUENCE: 69
atgaaccaaa gcaagcatga g                                                21

<210> SEQ ID NO 70
<211> LENGTH: 23
<212> TYPE: DNA
<213> ORGANISM: Homo sapiens

<400> SEQUENCE: 70
gagagaaggt ttgactgcca taa                                              23

<210> SEQ ID NO 71
<211> LENGTH: 22
<212> TYPE: DNA
<213> ORGANISM: Homo sapiens

<400> SEQUENCE: 71
gatttgctga accctattgg tg                                               22

<210> SEQ ID NO 72
<211> LENGTH: 25
<212> TYPE: DNA
<213> ORGANISM: Homo sapiens

<400> SEQUENCE: 72
tcagcagtta ctattctgtg actgg                                            25

<210> SEQ ID NO 73
<211> LENGTH: 23
<212> TYPE: DNA
<213> ORGANISM: Homo sapiens

<400> SEQUENCE: 73
gggaaagata gttgtgaatg agc                                              23

<210> SEQ ID NO 74
<211> LENGTH: 21
<212> TYPE: DNA
```

```
<213> ORGANISM: Homo sapiens

<400> SEQUENCE: 74
aaggaagttg tatggatcta g                                              21

<210> SEQ ID NO 75
<211> LENGTH: 19
<212> TYPE: DNA
<213> ORGANISM: Homo sapiens

<400> SEQUENCE: 75
cggccatgca gaaactgac                                                 19

<210> SEQ ID NO 76
<211> LENGTH: 21
<212> TYPE: DNA
<213> ORGANISM: Homo sapiens

<400> SEQUENCE: 76
caagaagcat aggcgtgtgt c                                              21

<210> SEQ ID NO 77
<211> LENGTH: 21
<212> TYPE: DNA
<213> ORGANISM: Homo sapiens

<400> SEQUENCE: 77
tctgagtgtt gctgctctgt g                                              21

<210> SEQ ID NO 78
<211> LENGTH: 24
<212> TYPE: DNA
<213> ORGANISM: Homo sapiens

<400> SEQUENCE: 78
gctaaattca tgcatcataa gctc                                           24

<210> SEQ ID NO 79
<211> LENGTH: 22
<212> TYPE: DNA
<213> ORGANISM: Homo sapiens

<400> SEQUENCE: 79
ggtgacactc cagaggcagt ag                                             22

<210> SEQ ID NO 80
<211> LENGTH: 23
<212> TYPE: DNA
<213> ORGANISM: Homo sapiens

<400> SEQUENCE: 80
gaggaataca caaacaccga cag                                            23

<210> SEQ ID NO 81
<211> LENGTH: 21
<212> TYPE: DNA
<213> ORGANISM: Homo sapiens

<400> SEQUENCE: 81
aaacaaatgg cacacgttct c                                              21

<210> SEQ ID NO 82
<211> LENGTH: 21
```

```
<212> TYPE: DNA
<213> ORGANISM: Homo sapiens

<400> SEQUENCE: 82
tggtgaaaga cgatggacaa g                                              21

<210> SEQ ID NO 83
<211> LENGTH: 21
<212> TYPE: DNA
<213> ORGANISM: Homo sapiens

<400> SEQUENCE: 83
tggattgtgc aattcctatg c                                              21

<210> SEQ ID NO 84
<211> LENGTH: 21
<212> TYPE: DNA
<213> ORGANISM: Homo sapiens

<400> SEQUENCE: 84
tttccatcct gcagaagaag c                                              21

<210> SEQ ID NO 85
<211> LENGTH: 22
<212> TYPE: DNA
<213> ORGANISM: Homo sapiens

<400> SEQUENCE: 85
ccctgaagtc cattaggtac gg                                             22

<210> SEQ ID NO 86
<211> LENGTH: 21
<212> TYPE: DNA
<213> ORGANISM: Homo sapiens

<400> SEQUENCE: 86
tcaaatatgg gctagatgcc a                                              21

<210> SEQ ID NO 87
<211> LENGTH: 26
<212> TYPE: DNA
<213> ORGANISM: Homo sapiens

<400> SEQUENCE: 87
ataaagattc aggcaatgtt tgttag                                         26

<210> SEQ ID NO 88
<211> LENGTH: 27
<212> TYPE: DNA
<213> ORGANISM: Homo sapiens

<400> SEQUENCE: 88
tgcaacattt ctaaagttac ctacttg                                        27

<210> SEQ ID NO 89
<211> LENGTH: 21
<212> TYPE: DNA
<213> ORGANISM: Homo sapiens

<400> SEQUENCE: 89
aatggctacg acccagttac c                                              21

<210> SEQ ID NO 90
```

-continued

<210> SEQ ID NO 90
<211> LENGTH: 21
<212> TYPE: DNA
<213> ORGANISM: Homo sapiens

<400> SEQUENCE: 90
aatgtctcac caatgccaga g                                           21

<210> SEQ ID NO 91
<211> LENGTH: 23
<212> TYPE: DNA
<213> ORGANISM: Homo sapiens

<400> SEQUENCE: 91
tgcaacagat aactcagatt gcc                                         23

<210> SEQ ID NO 92
<211> LENGTH: 21
<212> TYPE: DNA
<213> ORGANISM: Homo sapiens

<400> SEQUENCE: 92
tgacacaatg tcctattgcc a                                           21

<210> SEQ ID NO 93
<211> LENGTH: 21
<212> TYPE: DNA
<213> ORGANISM: Homo sapiens

<400> SEQUENCE: 93
attgcaagca agggttcaaa g                                           21

<210> SEQ ID NO 94
<211> LENGTH: 19
<212> TYPE: DNA
<213> ORGANISM: Homo sapiens

<400> SEQUENCE: 94
attgcaccat tgcactccc                                              19

<210> SEQ ID NO 95
<211> LENGTH: 21
<212> TYPE: DNA
<213> ORGANISM: Homo sapiens

<400> SEQUENCE: 95
caaagacaat ggctcctggt t                                           21

<210> SEQ ID NO 96
<211> LENGTH: 21
<212> TYPE: DNA
<213> ORGANISM: Homo sapiens

<400> SEQUENCE: 96
ttgtctttga ggcatcactg c                                           21

<210> SEQ ID NO 97
<211> LENGTH: 21
<212> TYPE: DNA
<213> ORGANISM: Homo sapiens

<400> SEQUENCE: 97
gttgggagta gatggagcct g                                           21

```
<210> SEQ ID NO 98
<211> LENGTH: 21
<212> TYPE: DNA
<213> ORGANISM: Homo sapiens

<400> SEQUENCE: 98
catcctggct aacggtgaaa c                                              21

<210> SEQ ID NO 99
<211> LENGTH: 21
<212> TYPE: DNA
<213> ORGANISM: Homo sapiens

<400> SEQUENCE: 99
aggcccttag cctctgtaag c                                              21

<210> SEQ ID NO 100
<211> LENGTH: 21
<212> TYPE: DNA
<213> ORGANISM: Homo sapiens

<400> SEQUENCE: 100
aagctcctga ggtgtagacg c                                              21

<210> SEQ ID NO 101
<211> LENGTH: 21
<212> TYPE: DNA
<213> ORGANISM: Homo sapiens

<400> SEQUENCE: 101
acgttctggt aaggacaagg g                                              21

<210> SEQ ID NO 102
<211> LENGTH: 21
<212> TYPE: DNA
<213> ORGANISM: Homo sapiens

<400> SEQUENCE: 102
aaatcatcca ttgcttggga c                                              21

<210> SEQ ID NO 103
<211> LENGTH: 20
<212> TYPE: DNA
<213> ORGANISM: Homo sapiens

<400> SEQUENCE: 103
agcccaaccc ttgtccttac                                                20

<210> SEQ ID NO 104
<211> LENGTH: 21
<212> TYPE: DNA
<213> ORGANISM: Homo sapiens

<400> SEQUENCE: 104
gaacctggtg caagaccaaa c                                              21

<210> SEQ ID NO 105
<211> LENGTH: 20
<212> TYPE: DNA
<213> ORGANISM: Homo sapiens

<400> SEQUENCE: 105
gtgagccaag attgtgccag                                                20
```

```
<210> SEQ ID NO 106
<211> LENGTH: 21
<212> TYPE: DNA
<213> ORGANISM: Homo sapiens

<400> SEQUENCE: 106
acctcatgac accaggagac c                                              21

<210> SEQ ID NO 107
<211> LENGTH: 21
<212> TYPE: DNA
<213> ORGANISM: Homo sapiens

<400> SEQUENCE: 107
actcacagtc agcaggtctg g                                              21

<210> SEQ ID NO 108
<211> LENGTH: 21
<212> TYPE: DNA
<213> ORGANISM: Homo sapiens

<400> SEQUENCE: 108
atcctagtgt ccgtgcgtag c                                              21

<210> SEQ ID NO 109
<211> LENGTH: 20
<212> TYPE: DNA
<213> ORGANISM: Homo sapiens

<400> SEQUENCE: 109
tgaggctcag agagaccgag                                                20

<210> SEQ ID NO 110
<211> LENGTH: 21
<212> TYPE: DNA
<213> ORGANISM: Homo sapiens

<400> SEQUENCE: 110
atgacagcat caatgaccca c                                              21

<210> SEQ ID NO 111
<211> LENGTH: 22
<212> TYPE: DNA
<213> ORGANISM: Homo sapiens

<400> SEQUENCE: 111
tctctaagcc agtgtgtgct tg                                             22

<210> SEQ ID NO 112
<211> LENGTH: 21
<212> TYPE: DNA
<213> ORGANISM: Homo sapiens

<400> SEQUENCE: 112
gttactgctg gcctctgttc c                                              21

<210> SEQ ID NO 113
<211> LENGTH: 20
<212> TYPE: DNA
<213> ORGANISM: Homo sapiens

<400> SEQUENCE: 113
cctgataaac gtgtggtggg                                                20
```

```
<210> SEQ ID NO 114
<211> LENGTH: 21
<212> TYPE: DNA
<213> ORGANISM: Homo sapiens

<400> SEQUENCE: 114
gctcagaaag ctgcacttca c                                         21

<210> SEQ ID NO 115
<211> LENGTH: 21
<212> TYPE: DNA
<213> ORGANISM: Homo sapiens

<400> SEQUENCE: 115
actggaaagc aagctagcac c                                         21

<210> SEQ ID NO 116
<211> LENGTH: 21
<212> TYPE: DNA
<213> ORGANISM: Homo sapiens

<400> SEQUENCE: 116
aggtgctagc ttgctttcca g                                         21

<210> SEQ ID NO 117
<211> LENGTH: 21
<212> TYPE: DNA
<213> ORGANISM: Homo sapiens

<400> SEQUENCE: 117
actcgaagag gaggacagag g                                         21

<210> SEQ ID NO 118
<211> LENGTH: 20
<212> TYPE: DNA
<213> ORGANISM: Homo sapiens

<400> SEQUENCE: 118
tgagctgaga ttgtgccacc                                           20

<210> SEQ ID NO 119
<211> LENGTH: 21
<212> TYPE: DNA
<213> ORGANISM: Homo sapiens

<400> SEQUENCE: 119
gagagagtcc tggtggtcct g                                         21

<210> SEQ ID NO 120
<211> LENGTH: 21
<212> TYPE: DNA
<213> ORGANISM: Homo sapiens

<400> SEQUENCE: 120
acagacttgg ctcttcccaa c                                         21

<210> SEQ ID NO 121
<211> LENGTH: 20
<212> TYPE: DNA
<213> ORGANISM: Homo sapiens

<400> SEQUENCE: 121
```
gttgggaaga gccaagtctg                                          20

<210> SEQ ID NO 122
<211> LENGTH: 20
<212> TYPE: DNA
<213> ORGANISM: Homo sapiens

<400> SEQUENCE: 122
gaagggtctc actcgctctg                                          20

<210> SEQ ID NO 123
<211> LENGTH: 21
<212> TYPE: DNA
<213> ORGANISM: Homo sapiens

<400> SEQUENCE: 123
gagccaactc actcatccct g                                        21

<210> SEQ ID NO 124
<211> LENGTH: 18
<212> TYPE: DNA
<213> ORGANISM: Homo sapiens

<400> SEQUENCE: 124
gcgagacacc caggttcc                                            18

<210> SEQ ID NO 125
<211> LENGTH: 22
<212> TYPE: DNA
<213> ORGANISM: Homo sapiens

<400> SEQUENCE: 125
tgatgaacca catggctatg ac                                       22

<210> SEQ ID NO 126
<211> LENGTH: 21
<212> TYPE: DNA
<213> ORGANISM: Homo sapiens

<400> SEQUENCE: 126
agcagtatgc cagtgtgttc g                                        21

<210> SEQ ID NO 127
<211> LENGTH: 21
<212> TYPE: DNA
<213> ORGANISM: Homo sapiens

<400> SEQUENCE: 127
acaggaccca tttccactca c                                        21

<210> SEQ ID NO 128
<211> LENGTH: 21
<212> TYPE: DNA
<213> ORGANISM: Homo sapiens

<400> SEQUENCE: 128
agacgatgag gtcatgcaag c                                        21

<210> SEQ ID NO 129
<211> LENGTH: 21
<212> TYPE: DNA
<213> ORGANISM: Homo sapiens

<400> SEQUENCE: 129
agaagacagg gagcgtgaaa c                                              21

<210> SEQ ID NO 130
<211> LENGTH: 20
<212> TYPE: DNA
<213> ORGANISM: Homo sapiens

<400> SEQUENCE: 130
cacgcacagg gtggacttag                                                20

<210> SEQ ID NO 131
<211> LENGTH: 20
<212> TYPE: DNA
<213> ORGANISM: Homo sapiens

<400> SEQUENCE: 131
ccttcctgaa cactgggacc                                                20

<210> SEQ ID NO 132
<211> LENGTH: 21
<212> TYPE: DNA
<213> ORGANISM: Homo sapiens

<400> SEQUENCE: 132
aaatatccca agagggccaa g                                              21

<210> SEQ ID NO 133
<211> LENGTH: 19
<212> TYPE: DNA
<213> ORGANISM: Homo sapiens

<400> SEQUENCE: 133
tgaggattgt gggagggag                                                 19

<210> SEQ ID NO 134
<211> LENGTH: 21
<212> TYPE: DNA
<213> ORGANISM: Homo sapiens

<400> SEQUENCE: 134
agcttgtagc tagcactggg c                                              21

<210> SEQ ID NO 135
<211> LENGTH: 21
<212> TYPE: DNA
<213> ORGANISM: Homo sapiens

<400> SEQUENCE: 135
aagttcagag ccagttccca g                                              21

<210> SEQ ID NO 136
<211> LENGTH: 21
<212> TYPE: DNA
<213> ORGANISM: Homo sapiens

<400> SEQUENCE: 136
cctgggatgg aggacagata g                                              21

<210> SEQ ID NO 137
<211> LENGTH: 21
<212> TYPE: DNA
<213> ORGANISM: Homo sapiens

```
<400> SEQUENCE: 137
cgaggttaca ccatctccga c                                              21

<210> SEQ ID NO 138
<211> LENGTH: 21
<212> TYPE: DNA
<213> ORGANISM: Homo sapiens

<400> SEQUENCE: 138
tcaaaggact gtgactgtgg c                                              21

<210> SEQ ID NO 139
<211> LENGTH: 19
<212> TYPE: DNA
<213> ORGANISM: Homo sapiens

<400> SEQUENCE: 139
ctggcctaag ctccctgtg                                                 19

<210> SEQ ID NO 140
<211> LENGTH: 19
<212> TYPE: DNA
<213> ORGANISM: Homo sapiens

<400> SEQUENCE: 140
ggtagcagga ctggatggg                                                 19

<210> SEQ ID NO 141
<211> LENGTH: 19
<212> TYPE: DNA
<213> ORGANISM: Homo sapiens

<400> SEQUENCE: 141
aggaggacct gccaccaac                                                 19

<210> SEQ ID NO 142
<211> LENGTH: 21
<212> TYPE: DNA
<213> ORGANISM: Homo sapiens

<400> SEQUENCE: 142
ggtgtctagc agtgcaacca g                                              21

<210> SEQ ID NO 143
<211> LENGTH: 19
<212> TYPE: DNA
<213> ORGANISM: Homo sapiens

<400> SEQUENCE: 143
ggttggagcg gctatgatg                                                 19

<210> SEQ ID NO 144
<211> LENGTH: 20
<212> TYPE: DNA
<213> ORGANISM: Homo sapiens

<400> SEQUENCE: 144
cagtaagtct gggaggcgtg                                                20

<210> SEQ ID NO 145
<211> LENGTH: 19
<212> TYPE: DNA
<213> ORGANISM: Homo sapiens
```

```
<400> SEQUENCE: 145
agcgggtagg gaatatggg                                                      19

<210> SEQ ID NO 146
<211> LENGTH: 20
<212> TYPE: DNA
<213> ORGANISM: Homo sapiens

<400> SEQUENCE: 146
atggtcctgt gaatgccatc                                                     20

<210> SEQ ID NO 147
<211> LENGTH: 20
<212> TYPE: DNA
<213> ORGANISM: Homo sapiens

<400> SEQUENCE: 147
accttgggaa atcccgaata                                                     20

<210> SEQ ID NO 148
<211> LENGTH: 20
<212> TYPE: DNA
<213> ORGANISM: Homo sapiens

<400> SEQUENCE: 148
gttggcaaat ggaaggattc                                                     20

<210> SEQ ID NO 149
<211> LENGTH: 21
<212> TYPE: DNA
<213> ORGANISM: Homo sapiens

<400> SEQUENCE: 149
gggtgaaaag ggtgttttgt t                                                   21

<210> SEQ ID NO 150
<211> LENGTH: 27
<212> TYPE: DNA
<213> ORGANISM: Homo sapiens

<400> SEQUENCE: 150
ggttttagtt tctagtacag ttgacca                                             27

<210> SEQ ID NO 151
<211> LENGTH: 22
<212> TYPE: DNA
<213> ORGANISM: Homo sapiens

<400> SEQUENCE: 151
gcaaaattgc tgatgagttt tt                                                  22

<210> SEQ ID NO 152
<211> LENGTH: 26
<212> TYPE: DNA
<213> ORGANISM: Homo sapiens

<400> SEQUENCE: 152
aagaaatgaa ttctctgaac tcttga                                              26

<210> SEQ ID NO 153
<211> LENGTH: 21
<212> TYPE: DNA
```

<213> ORGANISM: Homo sapiens

<400> SEQUENCE: 153
tgatgagcaa ggtggaaaat c                                              21

<210> SEQ ID NO 154
<211> LENGTH: 20
<212> TYPE: DNA
<213> ORGANISM: Homo sapiens

<400> SEQUENCE: 154
aaatcctgct gggattttg                                                 20

<210> SEQ ID NO 155
<211> LENGTH: 20
<212> TYPE: DNA
<213> ORGANISM: Homo sapiens

<400> SEQUENCE: 155
ccccatgggt aggtctttt                                                 20

<210> SEQ ID NO 156
<211> LENGTH: 20
<212> TYPE: DNA
<213> ORGANISM: Homo sapiens

<400> SEQUENCE: 156
tcagtccttc ctcagctcgt                                                20

<210> SEQ ID NO 157
<211> LENGTH: 23
<212> TYPE: DNA
<213> ORGANISM: Homo sapiens

<400> SEQUENCE: 157
gcttctctac actgccaaaa gtg                                            23

<210> SEQ ID NO 158
<211> LENGTH: 22
<212> TYPE: DNA
<213> ORGANISM: Homo sapiens

<400> SEQUENCE: 158
ttgtgggttt agaaagggta aa                                             22

<210> SEQ ID NO 159
<211> LENGTH: 20
<212> TYPE: DNA
<213> ORGANISM: Homo sapiens

<400> SEQUENCE: 159
tgagcatttc attggggaat                                                20

<210> SEQ ID NO 160
<211> LENGTH: 21
<212> TYPE: DNA
<213> ORGANISM: Homo sapiens

<400> SEQUENCE: 160
ttaaccaaat acgggagcag a                                              21

<210> SEQ ID NO 161
<211> LENGTH: 22

```
<212> TYPE: DNA
<213> ORGANISM: Homo sapiens

<400> SEQUENCE: 161
ggcaagaggg attaaaagat ga                                           22

<210> SEQ ID NO 162
<211> LENGTH: 20
<212> TYPE: DNA
<213> ORGANISM: Homo sapiens

<400> SEQUENCE: 162
ttggaaattc tggccgttta                                              20

<210> SEQ ID NO 163
<211> LENGTH: 20
<212> TYPE: DNA
<213> ORGANISM: Homo sapiens

<400> SEQUENCE: 163
tcttcagccc ctacgactgt                                              20

<210> SEQ ID NO 164
<211> LENGTH: 20
<212> TYPE: DNA
<213> ORGANISM: Homo sapiens

<400> SEQUENCE: 164
caattggatt tgtggtgtgg                                              20

<210> SEQ ID NO 165
<211> LENGTH: 20
<212> TYPE: DNA
<213> ORGANISM: Homo sapiens

<400> SEQUENCE: 165
ccaccttttc ctgctgtgtt                                              20

<210> SEQ ID NO 166
<211> LENGTH: 21
<212> TYPE: DNA
<213> ORGANISM: Homo sapiens

<400> SEQUENCE: 166
tggaacagag aggtaacagc a                                            21

<210> SEQ ID NO 167
<211> LENGTH: 23
<212> TYPE: DNA
<213> ORGANISM: Homo sapiens

<400> SEQUENCE: 167
tgctctgttt taatgtcgag tca                                          23

<210> SEQ ID NO 168
<211> LENGTH: 20
<212> TYPE: DNA
<213> ORGANISM: Homo sapiens

<400> SEQUENCE: 168
cagcttccca aagtgctagg                                              20

<210> SEQ ID NO 169
```

-continued

```
<210> SEQ ID NO 169
<211> LENGTH: 21
<212> TYPE: DNA
<213> ORGANISM: Homo sapiens

<400> SEQUENCE: 169
tctattggca catttatttc t                                              21

<210> SEQ ID NO 170
<211> LENGTH: 22
<212> TYPE: DNA
<213> ORGANISM: Homo sapiens

<400> SEQUENCE: 170
tttggagtcc agagtttaga cc                                             22

<210> SEQ ID NO 171
<211> LENGTH: 24
<212> TYPE: DNA
<213> ORGANISM: Homo sapiens

<400> SEQUENCE: 171
catctgatgc tgaggaaagt tctg                                           24

<210> SEQ ID NO 172
<211> LENGTH: 24
<212> TYPE: DNA
<213> ORGANISM: Homo sapiens

<400> SEQUENCE: 172
tgaatcttca tctgatggca ctga                                           24

<210> SEQ ID NO 173
<211> LENGTH: 23
<212> TYPE: DNA
<213> ORGANISM: Homo sapiens

<400> SEQUENCE: 173
aggaatggat aatcaagggc aca                                            23

<210> SEQ ID NO 174
<211> LENGTH: 27
<212> TYPE: DNA
<213> ORGANISM: Homo sapiens

<400> SEQUENCE: 174
ggataagcgt aattcttctg acagtgc                                        27

<210> SEQ ID NO 175
<211> LENGTH: 24
<212> TYPE: DNA
<213> ORGANISM: Homo sapiens

<400> SEQUENCE: 175
ccggtggtga acataagaaa tctg                                           24

<210> SEQ ID NO 176
<211> LENGTH: 24
<212> TYPE: DNA
<213> ORGANISM: Homo sapiens

<400> SEQUENCE: 176
cttgttcagt tccactgctg ccat                                           24
```

```
<210> SEQ ID NO 177
<211> LENGTH: 20
<212> TYPE: DNA
<213> ORGANISM: Homo sapiens

<400> SEQUENCE: 177
ccaatgcaag atgagccttc                                               20

<210> SEQ ID NO 178
<211> LENGTH: 22
<212> TYPE: DNA
<213> ORGANISM: Homo sapiens

<400> SEQUENCE: 178
cacaccagtg tcctggagat tt                                            22

<210> SEQ ID NO 179
<211> LENGTH: 23
<212> TYPE: DNA
<213> ORGANISM: Homo sapiens

<400> SEQUENCE: 179
tgccaaggtt gtcatgtgct tag                                           23

<210> SEQ ID NO 180
<211> LENGTH: 27
<212> TYPE: DNA
<213> ORGANISM: Homo sapiens

<400> SEQUENCE: 180
ccagcaatgt tggctttatc tgaactg                                       27

<210> SEQ ID NO 181
<211> LENGTH: 24
<212> TYPE: DNA
<213> ORGANISM: Homo sapiens

<400> SEQUENCE: 181
ttccttgttg agacccactg ctca                                          24

<210> SEQ ID NO 182
<211> LENGTH: 24
<212> TYPE: DNA
<213> ORGANISM: Homo sapiens

<400> SEQUENCE: 182
gctaattgta gggatgccgt ttcg                                          24

<210> SEQ ID NO 183
<211> LENGTH: 24
<212> TYPE: DNA
<213> ORGANISM: Homo sapiens

<400> SEQUENCE: 183
agtgtgagaa tgggtttgtg gagt                                          24

<210> SEQ ID NO 184
<211> LENGTH: 28
<212> TYPE: DNA
<213> ORGANISM: Homo sapiens

<400> SEQUENCE: 184
gggcttctat aaagcttgct aatctgtc                                      28
```

```
<210> SEQ ID NO 185
<211> LENGTH: 24
<212> TYPE: DNA
<213> ORGANISM: Homo sapiens

<400> SEQUENCE: 185
tgtgctttgg aggaggtagc caat                                          24

<210> SEQ ID NO 186
<211> LENGTH: 21
<212> TYPE: DNA
<213> ORGANISM: Homo sapiens

<400> SEQUENCE: 186
gtgccacatc ctgtctcttc c                                             21

<210> SEQ ID NO 187
<211> LENGTH: 20
<212> TYPE: DNA
<213> ORGANISM: Homo sapiens

<400> SEQUENCE: 187
aagagacagg atgtggcacg                                               20

<210> SEQ ID NO 188
<211> LENGTH: 21
<212> TYPE: DNA
<213> ORGANISM: Homo sapiens

<400> SEQUENCE: 188
tctcccagca gactcagttc c                                             21

<210> SEQ ID NO 189
<211> LENGTH: 21
<212> TYPE: DNA
<213> ORGANISM: Homo sapiens

<400> SEQUENCE: 189
caagggaaca ttctcctcac c                                             21

<210> SEQ ID NO 190
<211> LENGTH: 21
<212> TYPE: DNA
<213> ORGANISM: Homo sapiens

<400> SEQUENCE: 190
gagtccaggt tgactgatgg g                                             21

<210> SEQ ID NO 191
<211> LENGTH: 21
<212> TYPE: DNA
<213> ORGANISM: Homo sapiens

<400> SEQUENCE: 191
atgtcaggta tgaggcggat g                                             21

<210> SEQ ID NO 192
<211> LENGTH: 20
<212> TYPE: DNA
<213> ORGANISM: Homo sapiens

<400> SEQUENCE: 192
gtcagagcac tcagcccttg                                               20
```

<210> SEQ ID NO 193
<211> LENGTH: 21
<212> TYPE: DNA
<213> ORGANISM: Homo sapiens

<400> SEQUENCE: 193
taaccctccc acacacctct c                                              21

<210> SEQ ID NO 194
<211> LENGTH: 21
<212> TYPE: DNA
<213> ORGANISM: Homo sapiens

<400> SEQUENCE: 194
cgcctgttaa cctctgggta g                                              21

<210> SEQ ID NO 195
<211> LENGTH: 21
<212> TYPE: DNA
<213> ORGANISM: Homo sapiens

<400> SEQUENCE: 195
cagaggaagc agtagttcgg g                                              21

<210> SEQ ID NO 196
<211> LENGTH: 22
<212> TYPE: DNA
<213> ORGANISM: Homo sapiens

<400> SEQUENCE: 196
gggttagtgg gaaagaaagg ac                                             22

<210> SEQ ID NO 197
<211> LENGTH: 18
<212> TYPE: DNA
<213> ORGANISM: Homo sapiens

<400> SEQUENCE: 197
gagccctggg ttctgagc                                                  18

<210> SEQ ID NO 198
<211> LENGTH: 19
<212> TYPE: DNA
<213> ORGANISM: Homo sapiens

<400> SEQUENCE: 198
ccgtgagttg cagcttgat                                                 19

<210> SEQ ID NO 199
<211> LENGTH: 18
<212> TYPE: DNA
<213> ORGANISM: Homo sapiens

<400> SEQUENCE: 199
ggtctcagtc ccatcggc                                                  18

<210> SEQ ID NO 200
<211> LENGTH: 21
<212> TYPE: DNA
<213> ORGANISM: Homo sapiens

<400> SEQUENCE: 200
catccctaat cccgtacatg c                                              21

<210> SEQ ID NO 201
<211> LENGTH: 20
<212> TYPE: DNA
<213> ORGANISM: Homo sapiens

<400> SEQUENCE: 201
agatggagag gactccctgg                                                20

<210> SEQ ID NO 202
<211> LENGTH: 21
<212> TYPE: DNA
<213> ORGANISM: Homo sapiens

<400> SEQUENCE: 202
ccgtggctca taactctctc c                                              21

<210> SEQ ID NO 203
<211> LENGTH: 21
<212> TYPE: DNA
<213> ORGANISM: Homo sapiens

<400> SEQUENCE: 203
gtagagggtg agtgggtctg g                                              21

<210> SEQ ID NO 204
<211> LENGTH: 21
<212> TYPE: DNA
<213> ORGANISM: Homo sapiens

<400> SEQUENCE: 204
ctgaagctca ggaagggaaa g                                              21

<210> SEQ ID NO 205
<211> LENGTH: 21
<212> TYPE: DNA
<213> ORGANISM: Homo sapiens

<400> SEQUENCE: 205
aatctgaggt tgggtcacag g                                              21

<210> SEQ ID NO 206
<211> LENGTH: 21
<212> TYPE: DNA
<213> ORGANISM: Homo sapiens

<400> SEQUENCE: 206
cgaacctcac aaggcttaca g                                              21

<210> SEQ ID NO 207
<211> LENGTH: 21
<212> TYPE: DNA
<213> ORGANISM: Homo sapiens

<400> SEQUENCE: 207
aagctgaaga gggactggat g                                              21

<210> SEQ ID NO 208
<211> LENGTH: 21
<212> TYPE: DNA
<213> ORGANISM: Homo sapiens

<400> SEQUENCE: 208
tctgctttgg gacaaccata c							21

<210> SEQ ID NO 209
<211> LENGTH: 20
<212> TYPE: DNA
<213> ORGANISM: Homo sapiens

<400> SEQUENCE: 209
gcctccgtga ggctacatta							20

<210> SEQ ID NO 210
<211> LENGTH: 24
<212> TYPE: DNA
<213> ORGANISM: Homo sapiens

<400> SEQUENCE: 210
aaatctacag agttccctgt ttgc						24

<210> SEQ ID NO 211
<211> LENGTH: 25
<212> TYPE: DNA
<213> ORGANISM: Homo sapiens

<400> SEQUENCE: 211
tgaatacttg ttgaaatttc tccct						25

<210> SEQ ID NO 212
<211> LENGTH: 21
<212> TYPE: DNA
<213> ORGANISM: Homo sapiens

<400> SEQUENCE: 212
cggagatttg gatgttctcc t							21

<210> SEQ ID NO 213
<211> LENGTH: 21
<212> TYPE: DNA
<213> ORGANISM: Homo sapiens

<400> SEQUENCE: 213
caaactccga cttcgtgatc c							21

<210> SEQ ID NO 214
<211> LENGTH: 22
<212> TYPE: DNA
<213> ORGANISM: Homo sapiens

<400> SEQUENCE: 214
ttggttgatc tttgtcttcg tg						22

<210> SEQ ID NO 215
<211> LENGTH: 21
<212> TYPE: DNA
<213> ORGANISM: Homo sapiens

<400> SEQUENCE: 215
tgaattttcc ttttggggaa g							21

<210> SEQ ID NO 216
<211> LENGTH: 21
<212> TYPE: DNA
<213> ORGANISM: Homo sapiens

```
<400> SEQUENCE: 216
atgaatgaag gcaagctagg g                                            21

<210> SEQ ID NO 217
<211> LENGTH: 21
<212> TYPE: DNA
<213> ORGANISM: Homo sapiens

<400> SEQUENCE: 217
tgctgagatc agccaaattc a                                            21

<210> SEQ ID NO 218
<211> LENGTH: 27
<212> TYPE: DNA
<213> ORGANISM: Homo sapiens

<400> SEQUENCE: 218
aaagctagta atgtaagaag tttggga                                      27

<210> SEQ ID NO 219
<211> LENGTH: 23
<212> TYPE: DNA
<213> ORGANISM: Homo sapiens

<400> SEQUENCE: 219
atagactaat agtaatatag tgt                                          23

<210> SEQ ID NO 220
<211> LENGTH: 22
<212> TYPE: DNA
<213> ORGANISM: Homo sapiens

<400> SEQUENCE: 220
cgggagtttg acattgttct ga                                           22

<210> SEQ ID NO 221
<211> LENGTH: 20
<212> TYPE: DNA
<213> ORGANISM: Homo sapiens

<400> SEQUENCE: 221
ggccaccttc tatgttccaa                                              20

<210> SEQ ID NO 222
<211> LENGTH: 23
<212> TYPE: DNA
<213> ORGANISM: Homo sapiens

<400> SEQUENCE: 222
tttgagggta ggagaatgag aga                                          23

<210> SEQ ID NO 223
<211> LENGTH: 26
<212> TYPE: DNA
<213> ORGANISM: Homo sapiens

<400> SEQUENCE: 223
tctgttacca taggataaga aatgga                                       26

<210> SEQ ID NO 224
<211> LENGTH: 18
<212> TYPE: DNA
<213> ORGANISM: Homo sapiens
```

<400> SEQUENCE: 224
catgtgatgg cgtgatcc                                            18

<210> SEQ ID NO 225
<211> LENGTH: 22
<212> TYPE: DNA
<213> ORGANISM: Homo sapiens

<400> SEQUENCE: 225
ggaaaggcag taaaggtcat gc                                       22

<210> SEQ ID NO 226
<211> LENGTH: 21
<212> TYPE: DNA
<213> ORGANISM: Homo sapiens

<400> SEQUENCE: 226
taaatggaaa cttgcaccct g                                        21

<210> SEQ ID NO 227
<211> LENGTH: 21
<212> TYPE: DNA
<213> ORGANISM: Homo sapiens

<400> SEQUENCE: 227
tacccaggct ggtttcaatt c                                        21

<210> SEQ ID NO 228
<211> LENGTH: 23
<212> TYPE: DNA
<213> ORGANISM: Homo sapiens

<400> SEQUENCE: 228
gacatttgag caaagacctg aag                                      23

<210> SEQ ID NO 229
<211> LENGTH: 20
<212> TYPE: DNA
<213> ORGANISM: Homo sapiens

<400> SEQUENCE: 229
tccgtctagc caaacacacc                                          20

<210> SEQ ID NO 230
<211> LENGTH: 26
<212> TYPE: DNA
<213> ORGANISM: Homo sapiens

<400> SEQUENCE: 230
tctgtgatgt ataaaccgtg agtttc                                   26

<210> SEQ ID NO 231
<211> LENGTH: 29
<212> TYPE: DNA
<213> ORGANISM: Homo sapiens

<400> SEQUENCE: 231
catgattact actctaaacc catagaagg                                29

<210> SEQ ID NO 232
<211> LENGTH: 23
<212> TYPE: DNA

```
<213> ORGANISM: Homo sapiens

<400> SEQUENCE: 232
gaccaactgc ctcaaatagt agg                                          23

<210> SEQ ID NO 233
<211> LENGTH: 27
<212> TYPE: DNA
<213> ORGANISM: Homo sapiens

<400> SEQUENCE: 233
tttacttgtc aattacacct caataaa                                      27

<210> SEQ ID NO 234
<211> LENGTH: 21
<212> TYPE: DNA
<213> ORGANISM: Homo sapiens

<400> SEQUENCE: 234
tttggcttct ttagcccaat g                                            21

<210> SEQ ID NO 235
<211> LENGTH: 24
<212> TYPE: DNA
<213> ORGANISM: Homo sapiens

<400> SEQUENCE: 235
tgcagataca gaatccatat ttcg                                         24

<210> SEQ ID NO 236
<211> LENGTH: 23
<212> TYPE: DNA
<213> ORGANISM: Homo sapiens

<400> SEQUENCE: 236
tgtcaagcaa gttcttcatc agc                                          23

<210> SEQ ID NO 237
<211> LENGTH: 28
<212> TYPE: DNA
<213> ORGANISM: Homo sapiens

<400> SEQUENCE: 237
aaagatcatg tttgttacag tgcttaaa                                     28

<210> SEQ ID NO 238
<211> LENGTH: 21
<212> TYPE: DNA
<213> ORGANISM: Homo sapiens

<400> SEQUENCE: 238
ccatcttgat ttgaattccc g                                            21

<210> SEQ ID NO 239
<211> LENGTH: 20
<212> TYPE: DNA
<213> ORGANISM: Homo sapiens

<400> SEQUENCE: 239
agctgccttt gaccatgaag                                              20

<210> SEQ ID NO 240
<211> LENGTH: 25
```

<212> TYPE: DNA
<213> ORGANISM: Homo sapiens

<400> SEQUENCE: 240
agtttatcag gaagtaacac catcg                                      25

<210> SEQ ID NO 241
<211> LENGTH: 21
<212> TYPE: DNA
<213> ORGANISM: Homo sapiens

<400> SEQUENCE: 241
ggagcactaa gcgaggtaag c                                          21

<210> SEQ ID NO 242
<211> LENGTH: 21
<212> TYPE: DNA
<213> ORGANISM: Homo sapiens

<400> SEQUENCE: 242
ttgggcagtg ctaggaaaga g                                          21

<210> SEQ ID NO 243
<211> LENGTH: 21
<212> TYPE: DNA
<213> ORGANISM: Homo sapiens

<400> SEQUENCE: 243
agaaatcggt aagaggtggg c                                          21

<210> SEQ ID NO 244
<211> LENGTH: 20
<212> TYPE: DNA
<213> ORGANISM: Homo sapiens

<400> SEQUENCE: 244
ctgctcagat agcgatggtg                                            20

<210> SEQ ID NO 245
<211> LENGTH: 21
<212> TYPE: DNA
<213> ORGANISM: Homo sapiens

<400> SEQUENCE: 245
gggccagacc taagagcaat c                                          21

<210> SEQ ID NO 246
<211> LENGTH: 22
<212> TYPE: DNA
<213> ORGANISM: Homo sapiens

<400> SEQUENCE: 246
gaggaatccc aaagttccaa ac                                         22

<210> SEQ ID NO 247
<211> LENGTH: 21
<212> TYPE: DNA
<213> ORGANISM: Homo sapiens

<400> SEQUENCE: 247
cagtcagatc ctagcgtcga g                                          21

<210> SEQ ID NO 248

```
<211> LENGTH: 21
<212> TYPE: DNA
<213> ORGANISM: Homo sapiens

<400> SEQUENCE: 248
agggttggaa gtgtctcatg c                                              21

<210> SEQ ID NO 249
<211> LENGTH: 21
<212> TYPE: DNA
<213> ORGANISM: Homo sapiens

<400> SEQUENCE: 249
gtgtgggagg aaaggttatg c                                              21

<210> SEQ ID NO 250
<211> LENGTH: 22
<212> TYPE: DNA
<213> ORGANISM: Homo sapiens

<400> SEQUENCE: 250
ttaggtggtt tgtgacttgc ag                                             22

<210> SEQ ID NO 251
<211> LENGTH: 21
<212> TYPE: DNA
<213> ORGANISM: Homo sapiens

<400> SEQUENCE: 251
agatacgagc tttggaggtg g                                              21

<210> SEQ ID NO 252
<211> LENGTH: 20
<212> TYPE: DNA
<213> ORGANISM: Homo sapiens

<400> SEQUENCE: 252
cttcagggac ttcttggcag                                                20

<210> SEQ ID NO 253
<211> LENGTH: 24
<212> TYPE: DNA
<213> ORGANISM: Homo sapiens

<400> SEQUENCE: 253
tggtggtttc aactttattc actg                                           24

<210> SEQ ID NO 254
<211> LENGTH: 20
<212> TYPE: DNA
<213> ORGANISM: Homo sapiens

<400> SEQUENCE: 254
acctgagtgc ttgttgggtg                                                20

<210> SEQ ID NO 255
<211> LENGTH: 22
<212> TYPE: DNA
<213> ORGANISM: Homo sapiens

<400> SEQUENCE: 255
cccaagaatc agacaaccat tc                                             22
```

<210> SEQ ID NO 256
<211> LENGTH: 21
<212> TYPE: DNA
<213> ORGANISM: Homo sapiens

<400> SEQUENCE: 256
tctgtctttg ggaggagatg g                                              21

<210> SEQ ID NO 257
<211> LENGTH: 21
<212> TYPE: DNA
<213> ORGANISM: Homo sapiens

<400> SEQUENCE: 257
gaaaggccta gaaatgccac c                                              21

<210> SEQ ID NO 258
<211> LENGTH: 21
<212> TYPE: DNA
<213> ORGANISM: Homo sapiens

<400> SEQUENCE: 258
gaacacggtt ctggcagtct c                                              21

<210> SEQ ID NO 259
<211> LENGTH: 20
<212> TYPE: DNA
<213> ORGANISM: Homo sapiens

<400> SEQUENCE: 259
gagagggctg agggtgtctc                                                20

<210> SEQ ID NO 260
<211> LENGTH: 21
<212> TYPE: DNA
<213> ORGANISM: Homo sapiens

<400> SEQUENCE: 260
ctctgacagc aaaccagcct c                                              21

<210> SEQ ID NO 261
<211> LENGTH: 20
<212> TYPE: DNA
<213> ORGANISM: Homo sapiens

<400> SEQUENCE: 261
gtgcacaaca gagacagccc                                                20

<210> SEQ ID NO 262
<211> LENGTH: 21
<212> TYPE: DNA
<213> ORGANISM: Homo sapiens

<400> SEQUENCE: 262
tgaggaattg gaagtgtcac g                                              21

<210> SEQ ID NO 263
<211> LENGTH: 21
<212> TYPE: DNA
<213> ORGANISM: Homo sapiens

<400> SEQUENCE: 263
gactccaaca caacgcagat g                                              21

<210> SEQ ID NO 264
<211> LENGTH: 19
<212> TYPE: DNA
<213> ORGANISM: Homo sapiens

<400> SEQUENCE: 264
gactgcaggc agagggaag                    19

<210> SEQ ID NO 265
<211> LENGTH: 19
<212> TYPE: DNA
<213> ORGANISM: Homo sapiens

<400> SEQUENCE: 265
ttctgagtgc ctgtggtgc                    19

<210> SEQ ID NO 266
<211> LENGTH: 21
<212> TYPE: DNA
<213> ORGANISM: Homo sapiens

<400> SEQUENCE: 266
ctatggagcc ctgttctcag c                 21

<210> SEQ ID NO 267
<211> LENGTH: 21
<212> TYPE: DNA
<213> ORGANISM: Homo sapiens

<400> SEQUENCE: 267
gctgagaaca gggctccata g                 21

<210> SEQ ID NO 268
<211> LENGTH: 21
<212> TYPE: DNA
<213> ORGANISM: Homo sapiens

<400> SEQUENCE: 268
tgtgttactt ggcaggcact c                 21

<210> SEQ ID NO 269
<211> LENGTH: 20
<212> TYPE: DNA
<213> ORGANISM: Homo sapiens

<400> SEQUENCE: 269
ctaagcctcg gctgttctcc                   20

<210> SEQ ID NO 270
<211> LENGTH: 19
<212> TYPE: DNA
<213> ORGANISM: Homo sapiens

<400> SEQUENCE: 270
cgtggccttc tctcctctg                    19

<210> SEQ ID NO 271
<211> LENGTH: 19
<212> TYPE: DNA
<213> ORGANISM: Homo sapiens

<400> SEQUENCE: 271
cacctgcctg tcactctgc                    19

```
<210> SEQ ID NO 272
<211> LENGTH: 19
<212> TYPE: DNA
<213> ORGANISM: Homo sapiens

<400> SEQUENCE: 272
ctagcctgca gcttgtccc                                              19

<210> SEQ ID NO 273
<211> LENGTH: 21
<212> TYPE: DNA
<213> ORGANISM: Homo sapiens

<400> SEQUENCE: 273
gatctctcca tcctgaccct g                                           21

<210> SEQ ID NO 274
<211> LENGTH: 21
<212> TYPE: DNA
<213> ORGANISM: Homo sapiens

<400> SEQUENCE: 274
agctttggcc cttggtgata g                                           21

<210> SEQ ID NO 275
<211> LENGTH: 21
<212> TYPE: DNA
<213> ORGANISM: Homo sapiens

<400> SEQUENCE: 275
ctggacatga tggctcgata c                                           21

<210> SEQ ID NO 276
<211> LENGTH: 21
<212> TYPE: DNA
<213> ORGANISM: Homo sapiens

<400> SEQUENCE: 276
aggtgactgc accttccttt c                                           21

<210> SEQ ID NO 277
<211> LENGTH: 19
<212> TYPE: DNA
<213> ORGANISM: Homo sapiens

<400> SEQUENCE: 277
gggagcattc agcttgagg                                              19

<210> SEQ ID NO 278
<211> LENGTH: 20
<212> TYPE: DNA
<213> ORGANISM: Homo sapiens

<400> SEQUENCE: 278
gagaacaatg gtgctgaggc                                             20

<210> SEQ ID NO 279
<211> LENGTH: 21
<212> TYPE: DNA
<213> ORGANISM: Homo sapiens

<400> SEQUENCE: 279
```
caagccaaag acattctgca c    21

<210> SEQ ID NO 280
<211> LENGTH: 20
<212> TYPE: DNA
<213> ORGANISM: Homo sapiens

<400> SEQUENCE: 280
caggagaagg ctggttctcg    20

<210> SEQ ID NO 281
<211> LENGTH: 21
<212> TYPE: DNA
<213> ORGANISM: Homo sapiens

<400> SEQUENCE: 281
gttgatgcct ggcactttct c    21

<210> SEQ ID NO 282
<211> LENGTH: 20
<212> TYPE: DNA
<213> ORGANISM: Homo sapiens

<400> SEQUENCE: 282
gaacacgaaa ctgcacaggg    20

<210> SEQ ID NO 283
<211> LENGTH: 20
<212> TYPE: DNA
<213> ORGANISM: Homo sapiens

<400> SEQUENCE: 283
gctctgtgtt cctccctgtg    20

<210> SEQ ID NO 284
<211> LENGTH: 20
<212> TYPE: DNA
<213> ORGANISM: Homo sapiens

<400> SEQUENCE: 284
gctaacctgt cactcgcacc    20

<210> SEQ ID NO 285
<211> LENGTH: 21
<212> TYPE: DNA
<213> ORGANISM: Homo sapiens

<400> SEQUENCE: 285
tggaatggat ggtcttgtct g    21

<210> SEQ ID NO 286
<211> LENGTH: 21
<212> TYPE: DNA
<213> ORGANISM: Homo sapiens

<400> SEQUENCE: 286
ctcaggttcc gagcctaaca g    21

<210> SEQ ID NO 287
<211> LENGTH: 18
<212> TYPE: DNA
<213> ORGANISM: Homo sapiens

<400> SEQUENCE: 287

```
ctgtcccacc agctcacg                                                      18

<210> SEQ ID NO 288
<211> LENGTH: 21
<212> TYPE: DNA
<213> ORGANISM: Homo sapiens

<400> SEQUENCE: 288
ctggactacg agtgcaacct g                                                  21

<210> SEQ ID NO 289
<211> LENGTH: 20
<212> TYPE: DNA
<213> ORGANISM: Homo sapiens

<400> SEQUENCE: 289
agatcgtgtc tgaccgcaac                                                    20

<210> SEQ ID NO 290
<211> LENGTH: 21
<212> TYPE: DNA
<213> ORGANISM: Homo sapiens

<400> SEQUENCE: 290
cctctatgtc tgtgcactgg g                                                  21

<210> SEQ ID NO 291
<211> LENGTH: 17
<212> TYPE: DNA
<213> ORGANISM: Inovirus enterobacteria phage M13

<400> SEQUENCE: 291
gtaaaacgac ggccagt                                                       17
```